United States Patent
Kang et al.

(10) Patent No.: US 10,987,300 B2
(45) Date of Patent: *Apr. 27, 2021

(54) LONG LASTING COSMETIC COMPOSITIONS

(71) Applicant: Living Proof, Inc., Boston, MA (US)

(72) Inventors: Soo-Young Kang, Bedford, MA (US); Zhaoxia Ji, Natick, MA (US); Sara A. Turner, Boston, MA (US); Ling-Fang Tseng, Boston, MA (US); Dinara A. Villanueva, Boston, MA (US); Eric G. Spengler, Boston, MA (US)

(73) Assignee: Living Proof, Inc., Boston, MA (US)

( * ) Notice: Subject to any disclaimer, the term of this patent is extended or adjusted under 35 U.S.C. 154(b) by 101 days.

This patent is subject to a terminal disclaimer.

(21) Appl. No.: 16/128,620

(22) Filed: Sep. 12, 2018

(65) Prior Publication Data

US 2019/0076347 A1    Mar. 14, 2019

Related U.S. Application Data

(60) Provisional application No. 62/655,273, filed on Apr. 10, 2018, provisional application No. 62/557,823, filed on Sep. 13, 2017.

(51) Int. Cl.
| | | |
|---|---|---|
| *A61K 8/87* | (2006.01) | |
| *A61K 8/36* | (2006.01) | |
| *A61Q 5/06* | (2006.01) | |
| *A45D 7/06* | (2006.01) | |
| *A61Q 5/04* | (2006.01) | |
| *C08G 18/08* | (2006.01) | |
| *C08G 18/46* | (2006.01) | |
| *C08G 18/32* | (2006.01) | |
| *C08G 18/66* | (2006.01) | |
| *C08G 18/75* | (2006.01) | |
| *A61Q 5/00* | (2006.01) | |

(52) U.S. Cl.
CPC ............ *A61K 8/87* (2013.01); *A45D 7/06* (2013.01); *A61K 8/361* (2013.01); *A61Q 5/00* (2013.01); *A61Q 5/04* (2013.01); *A61Q 5/06* (2013.01); *C08G 18/0809* (2013.01); *C08G 18/3206* (2013.01); *C08G 18/3275* (2013.01); *C08G 18/46* (2013.01); *C08G 18/6655* (2013.01); *C08G 18/755* (2013.01); *A61K 2800/5426* (2013.01)

(58) Field of Classification Search
CPC .. A45D 7/06; A61K 2800/5426; A61K 8/361; A61K 8/87; A61Q 5/00; A61Q 5/04; A61Q 5/06; C08G 18/0809; C08G 18/3206; C08G 18/3275; C08G 18/46; C08G 18/6655; C08G 18/75; C08G 18/755

See application file for complete search history.

(56) References Cited

U.S. PATENT DOCUMENTS

| | | |
|---|---|---|
| 3,104,424 A | 9/1963 | Immel |
| 3,262,686 A | 7/1966 | Kraus et al. |
| 3,803,063 A | 4/1974 | Krentz, Jr. |
| 4,071,614 A | 1/1978 | Grimm, III |
| 4,455,146 A | 6/1984 | Noda et al. |
| 4,950,542 A | 8/1990 | Barker |
| 5,110,852 A | 5/1992 | Gogolewski et al. |
| 5,281,654 A | 1/1994 | Eisenhart et al. |
| 5,290,543 A | 3/1994 | Ounanian et al. |
| 5,335,373 A | 8/1994 | Dresdner, Jr. et al. |
| 5,357,636 A | 10/1994 | Dresdner, Jr. et al. |
| 5,534,265 A | 7/1996 | Fowler et al. |
| 5,534,348 A | 7/1996 | Miller et al. |
| 5,540,853 A | 7/1996 | Trinh et al. |
| 5,626,840 A | 5/1997 | Thomaides et al. |
| 5,637,291 A | 6/1997 | Bara et al. |
| 5,643,581 A | 7/1997 | Mougin et al. |
| 5,720,961 A | 2/1998 | Fowler et al. |
| 5,733,572 A | 3/1998 | Unger et al. |
| 5,807,540 A | 9/1998 | Junino et al. |
| 5,833,967 A | 11/1998 | Ramin |
| 5,846,551 A | 12/1998 | DaCunha et al. |
| 5,849,310 A | 12/1998 | Trinh et al. |
| 5,891,463 A | 4/1999 | Bello et al. |
| 5,900,457 A | 5/1999 | Duan et al. |
| 5,912,299 A | 6/1999 | Tomko et al. |
| 5,914,117 A | 6/1999 | Lavaud |
| 5,932,194 A | 8/1999 | Plessix et al. |
| 5,932,200 A | 8/1999 | Reich et al. |
| 5,993,972 A | 11/1999 | Reich et al. |
| 6,007,793 A | 12/1999 | Bhatt et al. |
| 6,084,051 A | 7/2000 | Blum et al. |

(Continued)

FOREIGN PATENT DOCUMENTS

| | | |
|---|---|---|
| BR | 102013022835 A2 | 8/2015 |
| CN | 1370185 A | 9/2002 |

(Continued)

OTHER PUBLICATIONS

Srivastava et al., Indian Application No. 148/DEL/2010. Bioreactor and Uses Thereof. Filed Jul. 29, 2011. 20 pages.
Teixeira et al., A case study of product engineering: Performance of microencapsulated perfumes on textile applications. AIChE Journal. Jun. 2011;58(6):1939-1950.
International Search Report and Written Opinion for Application No. PCT/US2017/021025, dated May 23, 2017.
International Search Report and Written Opinion for Application No. PCT/US2018/050538, dated Jan. 7, 2019, 17 pages.
Invitation to Pay Additional Fees for Application No. PCT/US2018/050546, dated Jan. 7, 2019, 15 pages.
U.S. Appl. No. 15/451,897, filed Mar. 7, 2017, 2017-0258700, Published.
U.S. Appl. No. 16/128,622, filed Sep. 12, 2018, Pending.

(Continued)

*Primary Examiner* — Anna R Falkowitz
(74) *Attorney, Agent, or Firm* — McCarter & English, LLP; Michael J. DeGrazia

(57) ABSTRACT

Provided herein are long lasting hair compositions, color enhancers, and markers for selecting the same.

16 Claims, 10 Drawing Sheets

(56) References Cited

U.S. PATENT DOCUMENTS

| | | | |
|---|---|---|---|
| 6,086,903 A | 7/2000 | Trinh et al. |
| 6,106,813 A | 8/2000 | Mondet et al. |
| 6,126,930 A | 10/2000 | Dubois et al. |
| 6,130,309 A | 10/2000 | Reich et al. |
| 6,132,704 A | 10/2000 | Bhatt et al. |
| 6,153,179 A | 11/2000 | Blankenburg et al. |
| 6,156,325 A | 12/2000 | Farer et al. |
| 6,221,344 B1 | 4/2001 | Ramin et al. |
| 6,238,651 B1 | 5/2001 | Bara |
| 6,254,876 B1 | 7/2001 | de la Poterie et al. |
| 6,277,386 B1 | 8/2001 | Kim et al. |
| 6,277,401 B1 | 8/2001 | Bello et al. |
| 6,291,580 B1 | 9/2001 | Kukkala et al. |
| 6,298,558 B1 | 10/2001 | Tseng et al. |
| 6,319,959 B1 | 11/2001 | Mougin et al. |
| 6,326,013 B1 | 12/2001 | Lemann et al. |
| 6,346,234 B1 | 2/2002 | Rollat et al. |
| 6,361,782 B1 | 3/2002 | Chevalier et al. |
| 6,365,697 B1 | 4/2002 | Kim et al. |
| 6,372,876 B1 | 4/2002 | Kim et al. |
| 6,403,070 B1 | 6/2002 | Pataut et al. |
| 6,403,107 B1 | 6/2002 | Lemann |
| 6,403,542 B1 | 6/2002 | Maurin et al. |
| 6,409,998 B1 | 6/2002 | Candau et al. |
| 6,433,073 B1 | 8/2002 | Kantner et al. |
| 6,465,534 B2 | 10/2002 | Fukuzawa et al. |
| 6,469,227 B1 | 10/2002 | Cooke et al. |
| 6,485,950 B1 | 11/2002 | Kumar et al. |
| 6,517,821 B1 | 2/2003 | Rollat et al. |
| 6,520,186 B2 | 2/2003 | Rollat et al. |
| 6,524,564 B1 | 2/2003 | Kim et al. |
| 6,524,597 B2 | 2/2003 | Kashimoto |
| 6,531,118 B1 | 3/2003 | Gonzalez et al. |
| 6,555,096 B2 | 4/2003 | Carrion et al. |
| 6,576,024 B1 | 6/2003 | Lang et al. |
| 6,576,702 B2 * | 6/2003 | Anderle ............ A61K 8/87 524/591 |
| 6,579,517 B1 | 6/2003 | Kim et al. |
| 6,592,881 B1 | 7/2003 | Fukuda et al. |
| 6,613,314 B1 | 9/2003 | Rollat et al. |
| 6,635,262 B2 | 10/2003 | Jourdan et al. |
| 6,641,804 B1 | 11/2003 | Ohta et al. |
| 6,682,748 B1 | 1/2004 | De La Poterie et al. |
| 6,689,345 B2 | 2/2004 | Jager Lezer |
| 6,692,729 B1 | 2/2004 | Asaoka et al. |
| 6,719,959 B1 | 4/2004 | Gonzalez et al. |
| 6,730,289 B2 | 5/2004 | Khoshdel |
| 6,750,291 B2 | 6/2004 | Kim et al. |
| 6,800,276 B2 | 10/2004 | Kim et al. |
| 6,830,758 B2 | 12/2004 | Nichols et al. |
| 6,884,853 B1 | 4/2005 | Asaoka et al. |
| 6,897,281 B2 | 5/2005 | Lubnin et al. |
| 6,927,254 B2 | 8/2005 | Melchiors et al. |
| 7,019,061 B2 | 3/2006 | Meffert et al. |
| 7,098,178 B2 | 8/2006 | Gerke et al. |
| 7,101,954 B2 | 9/2006 | Zofchak et al. |
| 7,160,553 B2 | 1/2007 | Gibbins et al. |
| 7,326,256 B2 | 2/2008 | Collard et al. |
| 7,348,299 B2 | 3/2008 | Keenan et al. |
| 7,445,770 B2 | 11/2008 | Berezkin et al. |
| 7,452,525 B1 | 11/2008 | Berezkin et al. |
| 7,481,996 B2 | 1/2009 | Ishii et al. |
| 7,659,233 B2 | 2/2010 | Hurley et al. |
| 7,700,082 B2 | 4/2010 | Mallo et al. |
| 7,740,832 B1 | 6/2010 | Rollat-Corvol et al. |
| 7,744,911 B2 | 6/2010 | Pechko et al. |
| RE41,615 E | 8/2010 | Kim et al. |
| 7,829,099 B2 | 11/2010 | Woeller et al. |
| 7,907,346 B2 | 3/2011 | Swarup et al. |
| 7,914,775 B2 | 3/2011 | Collard et al. |
| 7,959,903 B2 | 6/2011 | Candau et al. |
| 7,972,589 B2 | 7/2011 | Leighton et al. |
| 7,998,465 B2 | 8/2011 | De La Poterie et al. |
| 8,067,355 B2 | 11/2011 | Smets et al. |
| 8,258,093 B2 | 9/2012 | Van Dyke |
| 8,343,523 B2 | 1/2013 | Toreki et al. |
| 8,449,871 B2 | 5/2013 | Mougin et al. |
| 8,497,338 B2 | 7/2013 | Bai et al. |
| 8,623,388 B2 | 1/2014 | Rajaiah et al. |
| 8,629,213 B2 | 1/2014 | Hidalgo et al. |
| 8,679,050 B2 | 3/2014 | Nakamura |
| 8,679,465 B2 | 3/2014 | Malnou et al. |
| 8,734,772 B1 | 5/2014 | Zhou et al. |
| 8,741,333 B2 | 6/2014 | Zhang et al. |
| 8,784,854 B2 | 7/2014 | Choi et al. |
| 8,871,817 B2 | 10/2014 | Turk et al. |
| 8,882,902 B2 | 11/2014 | Suzuki et al. |
| 8,895,040 B2 | 11/2014 | Vondruska et al. |
| 8,956,160 B2 | 2/2015 | Willison et al. |
| 8,956,162 B2 | 2/2015 | De Vreese et al. |
| 9,016,221 B2 | 4/2015 | Brennan et al. |
| RE45,538 E | 6/2015 | Smets et al. |
| 9,079,152 B2 | 7/2015 | Markus et al. |
| 9,101,143 B2 | 8/2015 | Markus et al. |
| 9,102,783 B2 | 8/2015 | Yagi et al. |
| 9,175,125 B2 | 11/2015 | Turk et al. |
| 9,295,632 B1 | 3/2016 | Benn et al. |
| 9,340,650 B2 | 5/2016 | Wagner et al. |
| 9,393,218 B2 | 7/2016 | Zurdo Schroeder et al. |
| 2001/0031280 A1 | 10/2001 | Ferrari et al. |
| 2002/0034480 A1 | 3/2002 | Grimm et al. |
| 2002/0034486 A1 | 3/2002 | Midha et al. |
| 2002/0102222 A1 | 8/2002 | Carrion et al. |
| 2002/0107314 A1 | 8/2002 | Pinzon et al. |
| 2002/0114773 A1 | 8/2002 | Kanji et al. |
| 2002/0155962 A1 | 10/2002 | Cincotta et al. |
| 2002/0164297 A1 | 11/2002 | Ferrari et al. |
| 2002/0192273 A1 | 12/2002 | Buseman et al. |
| 2003/0026815 A1 | 2/2003 | Scott et al. |
| 2003/0064086 A1 | 4/2003 | Carrion et al. |
| 2003/0082126 A9 | 5/2003 | Pinzon et al. |
| 2003/0086886 A1 | 5/2003 | Midha |
| 2003/0086896 A1 | 5/2003 | Midha et al. |
| 2003/0099694 A1 | 5/2003 | Cevc et al. |
| 2003/0125427 A9 | 7/2003 | Pinzon et al. |
| 2003/0185780 A1 | 10/2003 | Ferrari et al. |
| 2003/0190345 A1 | 10/2003 | Cordes et al. |
| 2003/0191154 A1 | 10/2003 | Kalafsky et al. |
| 2003/0198659 A1 | 10/2003 | Hoffmann et al. |
| 2003/0203991 A1 | 10/2003 | Schottman et al. |
| 2004/0001798 A1 | 1/2004 | Perron et al. |
| 2004/0057914 A1 | 3/2004 | Bonda et al. |
| 2004/0071757 A1 | 4/2004 | Rolf |
| 2004/0086482 A1 | 5/2004 | Zofchak et al. |
| 2004/0120915 A1 | 6/2004 | Yang et al. |
| 2004/0131573 A1 | 7/2004 | Tang |
| 2004/0137028 A1 | 7/2004 | de la Poterie |
| 2004/0156804 A1 | 8/2004 | Poterie et al. |
| 2004/0166076 A1 | 8/2004 | Ferrari et al. |
| 2004/0166133 A1 | 8/2004 | Cavazzuti et al. |
| 2004/0176487 A1 | 9/2004 | Svedberg et al. |
| 2004/0186259 A1 | 9/2004 | Brehm et al. |
| 2004/0197286 A1 | 10/2004 | Robert et al. |
| 2004/0223987 A1 | 11/2004 | Ferrari |
| 2004/0228886 A1 | 11/2004 | Ding et al. |
| 2004/0247549 A1 | 12/2004 | Lu et al. |
| 2005/0008667 A1 | 1/2005 | Liechty et al. |
| 2005/0014674 A1 | 1/2005 | Liechty et al. |
| 2005/0043209 A1 | 2/2005 | Schmiedel et al. |
| 2005/0089540 A1 | 4/2005 | Uchiyama et al. |
| 2005/0118126 A1 | 6/2005 | Rollat et al. |
| 2005/0148753 A1 | 7/2005 | Nguyen-Kim et al. |
| 2005/0163741 A1 | 7/2005 | Zech |
| 2005/0169873 A1 | 8/2005 | Rollat et al. |
| 2005/0169874 A1 | 8/2005 | Zofchak et al. |
| 2005/0220740 A1 | 10/2005 | Dumousseaux |
| 2005/0220741 A1 | 10/2005 | Dumousseaux |
| 2005/0249691 A1 | 11/2005 | Monks et al. |
| 2005/0276831 A1 | 12/2005 | Dihora et al. |
| 2005/0287100 A1 | 12/2005 | Lebre |
| 2005/0287103 A1 | 12/2005 | Filippi et al. |
| 2005/0287182 A1 | 12/2005 | Monks et al. |
| 2005/0287183 A1 | 12/2005 | Lebre |
| 2006/0045890 A1 | 3/2006 | Gonzalez et al. |

(56) References Cited

U.S. PATENT DOCUMENTS

| | | |
|---|---|---|
| 2006/0045893 A1 | 3/2006 | Yu et al. |
| 2006/0051311 A1 | 3/2006 | Walter et al. |
| 2006/0073106 A1 | 4/2006 | Berg-Schultz et al. |
| 2006/0078519 A1 | 4/2006 | Lion et al. |
| 2006/0083762 A1 | 4/2006 | Brun et al. |
| 2006/0099550 A1 | 5/2006 | Faasse et al. |
| 2006/0120983 A1 | 6/2006 | Blin et al. |
| 2006/0134049 A1 | 6/2006 | Keenan et al. |
| 2006/0171984 A1 | 8/2006 | Cromack et al. |
| 2006/0193789 A1 | 8/2006 | Tamarkin et al. |
| 2006/0216250 A1 | 9/2006 | Schultz et al. |
| 2006/0233728 A1 | 10/2006 | Sagawa et al. |
| 2006/0281650 A1 | 12/2006 | Keenan et al. |
| 2006/0287219 A1 | 12/2006 | Dykstra et al. |
| 2007/0032605 A1 | 2/2007 | Harashina |
| 2007/0105977 A1 | 5/2007 | Gabriel et al. |
| 2007/0167565 A1 | 7/2007 | Rische et al. |
| 2007/0183992 A1 | 8/2007 | Dumousseaux et al. |
| 2007/0183997 A9 | 8/2007 | Lebre et al. |
| 2007/0189980 A1 | 8/2007 | Zhang et al. |
| 2007/0197704 A1 | 8/2007 | Walter et al. |
| 2007/0207222 A1 | 9/2007 | Yu et al. |
| 2007/0251026 A1 | 11/2007 | Lalleman et al. |
| 2008/0044373 A1 | 2/2008 | Ilekti et al. |
| 2008/0044445 A1 | 2/2008 | Rubin |
| 2008/0045985 A1 | 2/2008 | Gurtner et al. |
| 2008/0138368 A1 | 6/2008 | Lezer |
| 2008/0175875 A1 | 7/2008 | Sunkara |
| 2008/0254074 A1 | 10/2008 | Dussaud et al. |
| 2009/0049623 A1 | 2/2009 | Brown et al. |
| 2009/0056734 A1 | 3/2009 | Bacon |
| 2009/0061004 A1 | 3/2009 | Birkel et al. |
| 2009/0105195 A1 | 4/2009 | O'Brien |
| 2009/0112141 A1 | 4/2009 | Derr |
| 2009/0175928 A1 | 7/2009 | Maier et al. |
| 2009/0196842 A1 | 8/2009 | Zech et al. |
| 2009/0257960 A1 | 10/2009 | Kim et al. |
| 2009/0263338 A1 | 10/2009 | Rolland et al. |
| 2009/0285866 A1 | 11/2009 | Afriat et al. |
| 2010/0003198 A1 | 1/2010 | Stolmeier et al. |
| 2010/0233146 A1 | 9/2010 | McDaniel |
| 2010/0260687 A1 | 10/2010 | Yu et al. |
| 2010/0261629 A1 | 10/2010 | Smets et al. |
| 2010/0297036 A1 | 11/2010 | Feuillette |
| 2010/0325812 A1 | 12/2010 | Panandiker et al. |
| 2010/0325813 A1 | 12/2010 | Dykstra et al. |
| 2011/0010817 A1 | 1/2011 | Theberge et al. |
| 2011/0027211 A1 | 2/2011 | Viala et al. |
| 2011/0046286 A1 | 2/2011 | Lubnin et al. |
| 2011/0117042 A1 | 5/2011 | Viala et al. |
| 2011/0200927 A1 | 8/2011 | Jung et al. |
| 2011/0229430 A1 | 9/2011 | Hawkins et al. |
| 2011/0230474 A1 | 9/2011 | Grigorian et al. |
| 2011/0256311 A1 | 10/2011 | Mattos, Jr. |
| 2011/0272320 A1 | 11/2011 | Alwattari et al. |
| 2011/0274633 A1 | 11/2011 | Vu et al. |
| 2012/0255574 A1 | 10/2012 | Flohr et al. |
| 2013/0084256 A1 | 4/2013 | Li et al. |
| 2013/0161349 A1 | 6/2013 | Pfeiffenberger |
| 2013/0196849 A1 | 8/2013 | Combs et al. |
| 2013/0239344 A1 | 9/2013 | Stolarz, Jr. et al. |
| 2013/0239874 A1 | 9/2013 | Smith et al. |
| 2013/0261255 A1 | 10/2013 | Deyrail et al. |
| 2014/0010776 A1 | 1/2014 | Viala et al. |
| 2014/0044657 A1 | 2/2014 | Kelly et al. |
| 2014/0066496 A1 | 3/2014 | Gunari et al. |
| 2014/0086864 A1 | 3/2014 | Ishimori et al. |
| 2014/0105846 A1 | 4/2014 | Viala et al. |
| 2014/0142191 A1 | 5/2014 | De La Zerda et al. |
| 2014/0147396 A1 | 5/2014 | Sertchook et al. |
| 2014/0170327 A1 | 6/2014 | Dombrowski et al. |
| 2014/0219927 A1 | 8/2014 | Belluscio et al. |
| 2014/0248270 A1 | 9/2014 | Yu et al. |
| 2014/0248340 A1 | 9/2014 | Schwarzentruber et al. |
| 2014/0350269 A1 | 11/2014 | Eiji Borges Sato |
| 2015/0004117 A1* | 1/2015 | Tan .............. A61K 8/8147 424/70.16 |
| 2015/0007849 A1 | 1/2015 | Cajan et al. |
| 2015/0071978 A1 | 3/2015 | Chang |
| 2015/0118331 A1 | 4/2015 | Boam et al. |
| 2015/0119497 A1 | 4/2015 | Matsui et al. |
| 2015/0190450 A1 | 7/2015 | Chang |
| 2015/0238406 A1 | 8/2015 | Pohlmann et al. |
| 2015/0283041 A1 | 10/2015 | Benn et al. |
| 2015/0342845 A1 | 12/2015 | Hwang et al. |
| 2015/0344622 A1 | 12/2015 | Mukerjee et al. |
| 2016/0001099 A1 | 1/2016 | Castro et al. |
| 2016/0058678 A1 | 3/2016 | Smets et al. |
| 2016/0074311 A1 | 3/2016 | Massey-Brooker et al. |
| 2016/0143836 A1 | 5/2016 | Hayes et al. |
| 2016/0175233 A1 | 6/2016 | Benn |
| 2016/0175238 A1 | 6/2016 | Shin et al. |
| 2016/0184195 A1 | 6/2016 | Tan et al. |
| 2016/0220475 A1 | 8/2016 | Scherner et al. |
| 2017/0216188 A1 | 8/2017 | Bermudez Agudelo et al. |
| 2017/0258700 A1 | 9/2017 | Kang et al. |
| 2018/0000699 A1 | 1/2018 | Trahan |
| 2019/0076348 A1* | 3/2019 | Kang ............... A61K 8/0241 |
| 2019/0151221 A1 | 5/2019 | Kang et al. |
| 2019/0359786 A1 | 11/2019 | Trahan et al. |

FOREIGN PATENT DOCUMENTS

| | | |
|---|---|---|
| CN | 101130082 A | 2/2008 |
| CN | 101361701 A | 2/2009 |
| CN | 101980691 A | 2/2011 |
| CN | 102015803 A | 4/2011 |
| CN | 102895164 A | 1/2013 |
| CN | 104188877 A | 12/2014 |
| CN | 105213260 A | 1/2016 |
| CN | 105561841 A | 5/2016 |
| DE | 102015204154 A1 | 9/2016 |
| EP | 727981 A1 | 8/1996 |
| EP | 789550 A1 | 8/1997 |
| EP | 923927 A1 | 6/1999 |
| EP | 1058560 A1 | 12/2000 |
| EP | 1082953 A1 | 3/2001 |
| EP | 1090632 A1 | 4/2001 |
| EP | 1090633 A1 | 4/2001 |
| EP | 1092419 A1 | 4/2001 |
| EP | 1155676 A2 | 11/2001 |
| EP | 1161937 A2 | 12/2001 |
| EP | 1216690 A2 | 6/2002 |
| EP | 1218430 A1 | 7/2002 |
| EP | 1289363 A1 | 3/2003 |
| EP | 1417886 A1 | 5/2004 |
| EP | 1419759 A2 | 5/2004 |
| EP | 1481661 A2 | 12/2004 |
| EP | 1491179 A2 | 12/2004 |
| EP | 1579841 A1 | 9/2005 |
| EP | 1579849 A1 | 9/2005 |
| EP | 1598046 A1 | 11/2005 |
| EP | 1604634 A1 | 12/2005 |
| EP | 1707182 A1 | 10/2006 |
| EP | 1707183 A1 | 10/2006 |
| EP | 1773906 A1 | 4/2007 |
| EP | 1800671 A1 | 6/2007 |
| EP | 2209472 A1 | 7/2010 |
| EP | 2271304 A1 | 1/2011 |
| EP | 2391424 A2 | 12/2011 |
| EP | 2591772 A1 | 5/2013 |
| EP | 2611466 A2 | 7/2013 |
| EP | 2726067 A1 | 5/2014 |
| EP | 2858630 A1 | 4/2015 |
| EP | 2859794 A1 | 4/2015 |
| EP | 2867298 A1 | 5/2015 |
| EP | 2925296 A1 | 10/2015 |
| EP | 2995217 A1 | 3/2016 |
| EP | 3020454 A1 | 5/2016 |
| FR | 2801209 A1 | 5/2001 |
| FR | 2835529 A1 | 8/2003 |
| FR | 2892931 A1 | 5/2007 |
| FR | 2902655 A1 | 12/2007 |
| FR | 2940093 A1 | 6/2010 |

(56) References Cited

FOREIGN PATENT DOCUMENTS

| | | |
|---|---|---|
| FR | 2957347 A1 | 9/2011 |
| FR | 2967062 A1 | 5/2012 |
| JP | H06362 A | 1/1994 |
| JP | H1080973 A | 3/1998 |
| JP | 2004-256694 A | 9/2004 |
| JP | 2006-290845 A | 10/2006 |
| JP | 2010-132568 A | 6/2010 |
| JP | 2011-173851 A | 9/2011 |
| JP | 2016-094362 A | 5/2016 |
| KR | 20080064230 A | 7/2008 |
| KR | 20090058294 A | 6/2009 |
| KR | 20090081582 A | 7/2009 |
| KR | 20110062277 A | 6/2011 |
| KR | 20140078356 A | 6/2014 |
| KR | 20140093349 A | 7/2014 |
| WO | 1989/007959 A1 | 9/1989 |
| WO | 1991/001970 A2 | 2/1991 |
| WO | 1994/13354 A1 | 6/1994 |
| WO | 1998/13025 A1 | 4/1998 |
| WO | 1998/26751 A1 | 6/1998 |
| WO | 1998/26756 A1 | 6/1998 |
| WO | 1999/12519 A1 | 3/1999 |
| WO | 1999/55288 A1 | 11/1999 |
| WO | 1999/55290 A1 | 11/1999 |
| WO | 1999/55291 A1 | 11/1999 |
| WO | 1999/55292 A1 | 11/1999 |
| WO | 1999/56708 A1 | 11/1999 |
| WO | 2000/14091 A1 | 3/2000 |
| WO | 2000/016752 A2 | 3/2000 |
| WO | 2000/018367 A1 | 4/2000 |
| WO | 2000/027350 A1 | 5/2000 |
| WO | 2000/40628 A1 | 7/2000 |
| WO | 2001/003652 A2 | 1/2001 |
| WO | 2001/024768 A2 | 4/2001 |
| WO | 2001/068037 A2 | 9/2001 |
| WO | 2001/078691 A1 | 10/2001 |
| WO | 2001/087065 A1 | 11/2001 |
| WO | 2001/094438 A1 | 12/2001 |
| WO | 2002/007699 A1 | 1/2002 |
| WO | 2002/039961 A1 | 5/2002 |
| WO | 2002/039964 A1 | 5/2002 |
| WO | 2002/043490 A1 | 6/2002 |
| WO | 2002/043491 A1 | 6/2002 |
| WO | 2002/045663 A1 | 6/2002 |
| WO | 2002/047620 A2 | 6/2002 |
| WO | 2002/047624 A1 | 6/2002 |
| WO | 2002/047626 A1 | 6/2002 |
| WO | 2002/047628 A1 | 6/2002 |
| WO | 2002/047657 A2 | 6/2002 |
| WO | 2002/047658 A2 | 6/2002 |
| WO | 2002/054997 A1 | 7/2002 |
| WO | 2002/055034 A2 | 7/2002 |
| WO | 2002/072045 A2 | 9/2002 |
| WO | 2003/028678 A1 | 4/2003 |
| WO | 2003/094870 A1 | 11/2003 |
| WO | 2004/110401 A2 | 12/2004 |
| WO | 2005/014777 A2 | 2/2005 |
| WO | 2005/017134 A2 | 2/2005 |
| WO | 2005/092963 A1 | 10/2005 |
| WO | 2006/015718 A1 | 2/2006 |
| WO | 2006/062740 A2 | 6/2006 |
| WO | 2006/127883 A2 | 11/2006 |
| WO | 2006/131403 A1 | 12/2006 |
| WO | 2007/057059 A1 | 5/2007 |
| WO | 2007/070643 A2 | 6/2007 |
| WO | 2007/071886 A2 | 6/2007 |
| WO | 2007/077029 A1 | 7/2007 |
| WO | 2007/145395 A1 | 12/2007 |
| WO | 2008/006677 A1 | 1/2008 |
| WO | 2008/006687 A1 | 1/2008 |
| WO | 2008/024408 A2 | 2/2008 |
| WO | 2008/125406 A2 | 10/2008 |
| WO | 2008/133982 A2 | 11/2008 |
| WO | 2008/148809 A1 | 12/2008 |
| WO | 2009/014347 A2 | 1/2009 |
| WO | 2009/053594 A2 | 4/2009 |
| WO | 2010/003138 A1 | 1/2010 |
| WO | 2010/006442 A1 | 1/2010 |
| WO | 2010/037402 A1 | 4/2010 |
| WO | 2010/076483 A1 | 7/2010 |
| WO | 2010/079468 A2 | 7/2010 |
| WO | 2010/086754 A2 | 8/2010 |
| WO | 2010/129299 A2 | 11/2010 |
| WO | 2011/016140 A1 | 2/2011 |
| WO | 2011/016531 A1 | 2/2011 |
| WO | 2011/075556 A1 | 6/2011 |
| WO | 2011/089709 A1 | 7/2011 |
| WO | 2011/126978 A1 | 10/2011 |
| WO | 2011/140330 A2 | 11/2011 |
| WO | 2012/037445 A2 | 3/2012 |
| WO | 2012/063947 A1 | 5/2012 |
| WO | 2012/087510 A1 | 6/2012 |
| WO | 2012/117013 A1 | 9/2012 |
| WO | 2012/121704 A1 | 9/2012 |
| WO | 2012/168102 A2 | 12/2012 |
| WO | 2013/068478 A1 | 5/2013 |
| WO | 2013/071079 A1 | 5/2013 |
| WO | 2013/149323 A1 | 10/2013 |
| WO | 2014/001574 A1 | 1/2014 |
| WO | 2014/001985 A1 | 1/2014 |
| WO | 2014/014139 A1 | 1/2014 |
| WO | 2014/105676 A1 | 7/2014 |
| WO | 2014/176515 A2 | 10/2014 |
| WO | 2015/020060 A1 | 2/2015 |
| WO | 2015/028417 A1 | 3/2015 |
| WO | 2015/028418 A1 | 3/2015 |
| WO | 2015/028421 A1 | 3/2015 |
| WO | 2015/028424 A1 | 3/2015 |
| WO | 2015/051139 A1 | 4/2015 |
| WO | 2015/188335 A1 | 12/2015 |
| WO | 2016/016315 A1 | 2/2016 |
| WO | 2016/058958 A1 | 4/2016 |
| WO | 2016/069396 A2 | 5/2016 |
| WO | 2016/074683 A1 | 5/2016 |
| WO | 2016/087948 A2 | 6/2016 |
| WO | 2016/096928 A1 | 6/2016 |
| WO | 2016/100885 A1 | 6/2016 |
| WO | 2016/115257 A2 | 7/2016 |
| WO | 2016/138249 A1 | 9/2016 |
| WO | 2017/155906 A1 | 9/2017 |

OTHER PUBLICATIONS

U.S. Appl. No. 16/195,584, filed Nov. 19, 2018, Pending.
Adina, Natpure Hollowbead. Adina Cosmetic Ingredients Ltd., retrieved online at: http://www.cosmeticingredients.co.uk/ingredient/natpure-hollowbead. 2 pages, (2015).
AkzoNobel, Product Specification for Expancel Microspheres. www.expancel.com, 2 pages, (2011).
Araujo et al., Techniques for reducing residual monomer content in polymers: a review. Polymer Engineering and Science. 64 pages, Jul. 1, 2002.
Lochhead et al., Polymers in Cosmetics: Recent Advances. From film-formers to rheology modifiers, polymers serve various functions. Retrieved online at: https://www.happi.com/contents/view_features/2005-11-15/polymers-in-cosmetics-recent-advances. 12 pages, Nov. 15, 2005.
Copending U.S. Appl. No. 16/348,644, filed May 9, 2019.

\* cited by examiner

Conditioner with 0%
LP Cationic WBPU

Conditioner with 5%
LP Cationic WBPU

LONG LASTING COSMETIC COMPOSITIONS

RELATED APPLICATIONS

This application claims priority to U.S. Provisional Application No. 62/655,273, filed Apr. 10, 2018 and U.S. Provisional Application No. 62/557,823, filed Sep. 13, 2017, the entire contents of each of which are incorporated herein by reference.

BACKGROUND

Polyurethanes are a well-known class of synthetic polymers with broad utility in multiple industries. This versatility is derived from the ability to prepare polyurethanes from a large and diverse set of potential monomers. These diverse monomer options allow the realization of an equally diverse set of physical properties. Hence, the resulting polyurethanes can be in many different forms including e.g., soft foams, elastomers, adhesive films, or hard plastics, and can be used in many different types of products including bedding, foot wear, adhesives, and automobile parts. Among these many forms of polyurethanes, waterborne polyurethanes (WBPUs) have been used as film forming agents in commercially available personal care products.

A problem with the use of WBPUs has been the lack of performance and overall consistency in application. For example, common polyurethane products such as Luviset® P.U.R (Polyurethane-1), DynamX, and DynamX/H$_2$O (Polyurethane-14 and AMP-Acrylates Copolymer) lack elasticity. This leads to an undesirable stiff feeling when applied to hair. Avalure UR 450 (PPG-17/IPDI/DMPA Copolymer), Baycusan C1004 (Polyurethane-35), Baycusan C1008 (Polyurethane-48), and Polyderm PE/PA ED (Polyurethane-58), on the other hand, are very flexible (i.e., do not lack elasticity). These products, however, have poor initial curl hold and elicit a gummy feeling. Other problems associated with the use of WBPUs include e.g., flaking upon touching or combing (e.g., dusty micro-flakes shown on hair fibers); undesirable tactile feelings upon touch (e.g., brittle, stiff, or tacky, gummy); poor humidity resistance (e.g., styling resins absorb moisture and weigh down hair resulting in a loss of style); lack of movement (e.g., plastic-like mold shape; hair curls don't move with motion; can't easily comb through; gummy; lack of bounciness); and short-lived hair styles (e.g., hair styles, curls, waves, etc. don't last long—on average styles typically last less than a half day).

There is therefore a need for improved and more consistent WBPU-based personal care products including e.g., ones that provide enhanced hold, high humidity curl retention, and/or positive sensory attributes.

SUMMARY

A specific combination of selection markers for cationic polyurethanes have now been identified that result in cosmetic compositions (e.g., hair products) which have substantially improved performance and which can be used in a variety of applications. Markers for these cationic polymers include e.g., a Young's modulus above 150 MPa, an elongation at break from about 15% to about 300%, and a moisture uptake of less than 10%.

In one aspect, the disclosed cationic polyurethanes can be used in a two-wave hair styling process comprising anionic polyurethanes. Applying and fixing the disclosed cationic polyurethanes to the hair prior to the application of anionic polyurethanes was found to enhance hold, high humidity curl retention, and positive sensory attributes. See e.g., FIG. 2 to FIG. 6.

In another aspect, the disclosed cationic polyurethanes can serve as additives for conditioners or leave-in-conditioners. When used in this manner, the disclosed cationic polyurethanes were found to provide better hold, improve stylability, minimize flyaways, and to sustain natural curl enhancement. See e.g., FIG. 7 to FIG. 10.

DETAILED DESCRIPTION

1. Definitions

Figure 1:
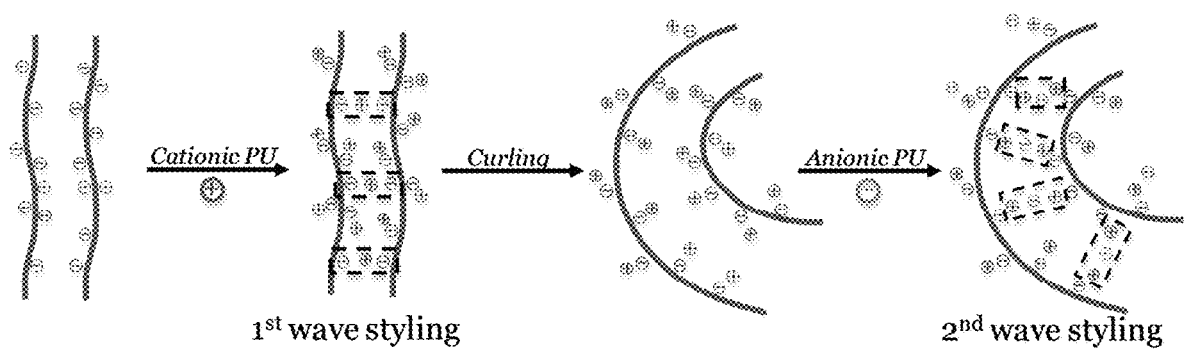
FIG. 1 is an illustration of a two-wave styling process using the cationic polyurethanes described herein.

A composition, process, or method described herein that "consists essentially of" a cationic polyurethane and other components means that the recited cationic polyurethane is the only polyurethane present in the recited composition, process, or method. Thus, "consists essentially of" or "consisting essentially of" is open ended for all terms except for the inclusion of additional polyurethanes, i.e., only the recited cationic polyurethane is present.

A composition, process, or method described herein that "consists of" a cationic polyurethane and other components means that only the recited components are present. In other words, "consisting of" excludes any element, step, or ingredient not specified. "Consists of" and "consisting of" are used interchangeably.

"Comprising" is inclusive or open-ended and does not exclude additional, un-recited elements or method steps.

As used herein, "cationic polyurethanes" refer to thermoplastic polymers comprising carbamate (urethane) groups and which bear an overall net positive charge at pH<7. In some aspects, the cationic polyurethanes described herein bear an overall net positive charge at pH from about 3.7 to about 6.5, from about 3.7 to about 6.0, or from about 3.7 to about 5.5. Unless otherwise specified, cationic polyurethanes, when used herein, include amphoteric/cationic polyurethanes. In one aspect, however, cationic polyurethanes do not encompass amphoteric/cationic polyurethanes.

As used herein, "anionic polyurethanes" refer to thermoplastic polymers comprising carbamate (urethane) groups and which bear an overall net negative charge at pH≥7. Unless otherwise specified, anionic polyurethanes, when used herein, include amphoteric/anionic polyurethanes. In one aspect, however, anionic polyurethanes do not encompass amphoteric/anionic polyurethanes.

As used herein, "amphoteric polyurethanes" refer to thermoplastic polymers comprising carbamate (urethane) groups and which can act as a cationic or anionic polyurethane. An "amphoteric/cationic polyurethane" means that the described amphoteric species is one which is acting as an acid under the defined methods and/or conditions. Similarly, an "amphoteric/anionic polyurethane" means that the described amphoteric species is one which is acting as a base under the defined methods and/or conditions.

"Young's modulus (or the modulus of elasticity, tensile modulus)" is a measure of the stiffness of a solid polymer film. Young's modulus, E, can be calculated by dividing the tensile stress by the extensional strain in the elastic (initial, linear) portion of the stress-strain curve. The Young's modulus of the cationic polyurethane can be determined by a protocol defined to measure mechanical properties, and is developed in reference to ASTM D638, ASTM D412, test guidelines as described below in Example 2.

The "elongation at break (also known as fracture strain, ultimate elongation)" is the ratio between changed length and initial length after breakage of the solid polymer film. The elongation at break of the cationic polyurethane can be determined by a protocol defined to measure mechanical properties, and is developed in reference to ASTM D638, ASTM D412, test guidelines as described below in Example 2.

The "moisture uptake" is the measure of water adsorbed by the solid polymer film. The method for determining the moisture uptake of the solid polymer film is provided in Example 3.

The "sensory score" is determined by the performance of the hair fixative. In particular, the tress with the composition applied is blow dried for 90 seconds. The tresses are prepared in duplicate and blinded randomly and evaluated for natural feeling and overall sensory attributes on a scale of −2 to 2 by trained sensory analysts under blinded conditions. Sensory analysts are licensed hair stylists and cosmetic scientists with significant long-term experience evaluating sensory attributes of hair. Sensory analysts assign a score of −2 to tresses deemed entirely undesirable, a score of +2 to entirely soft, natural feeling and appearing hair, and intermediate scores between these two extremes.

2. Selection Markers

Provided herein are specific combinations of WBPU properties that have been found to result in cosmetic compositions (e.g., hair products) having substantially improved performance. Those properties include e.g., a combination of certain mechanical properties, a combination of certain chemical properties, or a combination of both mechanical and chemical properties.

Young's Modulus, Elongation at Break, and Moisture Uptake

The combination of mechanical properties described herein include the Young's modulus (e.g., above 150 MPa), the elongation at break (e.g., from about 15% to about 300%), and hydrophobicity (moisture uptake, e.g., less than 10%).

In one aspect, the Young's modulus of the cationic polyurethane should be above about 150 MPa. For example, the Young's modulus of the cationic polyurethane in the disclosed compositions may be above about 160 MPa, above about 170 MPa, above about 180 MPa, above about 190 MPa, above about 200 MPa, above about 210 MPa, above about 220 MPa, above about 230 MPa, above about 240 MPa, above about 250 MPa, above about 260 MPa, above about 270 MPa, above about 280 MPa, above about 290 MPa, above about 300 MPa, above about 310 MPa, above about 320 MPa, above about 330 MPa, above about 340 MPa, above about 350 MPa, above about 360 MPa, above about 370 MPa, above about 380 MPa, above about 390 MPa, above about 400 MPa, above about 410 MPa, above about 420 MPa, above about 430 MPa, above about 440 MPa, above about 450 MPa, above about 460 MPa, above about 470 MPa, above about 480 MPa, above about 490 MPa, above about 500 MPa, above about 510 MPa, above about 520 MPa, above about 530 MPa, above about 540 MPa, or above 550 MPa. In other aspects, the Young's modulus of the cationic polyurethane should be between about 150 MPa and about 500 MPa. For example, the Young's modulus of the cationic polyurethane in the disclosed compositions may be between about 150 MPa and about 400 MPa, between about 150 MPa and about 350 MPa, between about 170 MPa and about 390 MPa, between about 180 MPa and about 320 MPa, between about 190 MPa and about 300 MPa, between about 200 MPa and about 290 MPa, or between about 210 MPa and about 280 MPa.

In one aspect, the elongation at break of the cationic polyurethane should be from about 15% to about 300%. For example, the elongation at break of the cationic polyurethane in the disclosed composition may be from about 20% to about 300%, from about 25% to about 300%, from about 40% to about 280%, from about 100% to about 280%, from about 100% to about 250%, from about 150% to about 250%, from about 200% to about 250%, from about 210% to about 250%, about 30% to about 150%, from about 15% to about 150%, from about 150% to about 300%, from about 50% to about 250%; from about 75% to about 225%, or from about 100 to about 200%. The elongation break may be optionally combined with one or more of the Young's modulus values described in the paragraph above or any one of the Young's modulus values described in the remainder of the disclosure.

In one aspect, the moisture uptake of the cationic polyurethane should be less than about 10%. For example, the moisture uptake of the cationic polyurethane in the disclosed compositions may be less than about 9.5%, less than about 9%, less than about 8.5%, less than about 8%, less than about 7.5%, less than about 7%, less than about 6.5%, less than about 6%, less than about 5.5%, less than about 5%, less than about 4.5%, less than about 4%, less than about 3.5%, less than about 3%, less than about 2.5%, less than about 2%, less than about 1.5%, less than about 1%, less than about 0.5%, or is about 0%. In one aspect, the moisture uptake of the cationic polyurethane in the disclosed compositions should be from about 0% to about 10%. For example, the moisture uptake may be from about 0% to about 8%, from about 2% to about 8%, or from about 3% to about 7%. The moisture uptake may be optionally combined with one or more of the Young's modulus values, one or more of the elongation break values, or both as described in the paragraphs above or in the remainder of the disclosure.

As shown in the Exemplification section below, cationic polyurethanes having the Young's modulus, elongation at break, and moisture uptake described above have improved performance (e.g., enhanced hold, high humidity curl retention, positive sensory attributes, improved stylability, natural curl enhancement, and minimization of flyaways.

Additional Indicators

In addition to the Young's modulus, elongation at break, and moisture uptake, other indicators may be used to identify the capability of cationic polyurethanes to provide long lasting, moisture-resistant hold hair product with favorable sensory attributes. Such indicators include e.g., change in tress length and sensory score.

Thus, in certain aspects, the cationic polyurethane may be selected such that the composition, after being applied to a curled hair tress and dried thereon, provides less than about 80% change in tress length as measured by the high humidity mechanical stress test. For example, the cationic polyurethane may be selected such that the composition, after being applied to a curled hair tress and dried thereon, provides less than about 75%, about 70%, about 65%, about 60%, about 55%, about 50%, about 45%, about 40%, about 35%, about 30%, about 25%, about 20%, about 15%, about 10%, about 5%, or about 0% change in tress length as measured by the high humidity mechanical stress test. The change in tress length as described herein may also be combined with any one of the Young's modulus values, elongation at break values, and moisture uptake values described above and herein.

In other aspects, the cationic polyurethane may be selected such that the composition, after being applied to a hair tress and dried thereon, provides a sensory score of at least about 0. For example, the cationic polyurethanes in the disclosed compositions may be selected such that the composition, after being applied to a hair tress and dried thereon, provides a sensory score of at least about 0.1, about 0.2, about 0.3, about 0.4, about 0.5, about 0.6, about 0.7, about 0.8, about 0.9, about 1.0, about 1.1, about 1.2, about 1.3, about 1.4, or about 1.5. The sensory score feature as described herein may also be combined with any one of the change in tress length values, the Young's modulus values, the elongation at break values, and the moisture uptake values described above and herein.

As shown in the Exemplification section below, cationic polyurethanes having the Young's modulus, elongation at break, and moisture uptake described above, and optionally one or more of the alternative indicators (e.g., sensory score, change in tress length, etc.) provide hair styling products with improved mechanical properties, sensory properties and performance.

3. Compositions

Provided herein are compositions (e.g., hair treatment compositions) comprising a cationic polyurethane having a Young's modulus above 150 MPa, an elongation at break from about 15% to about 300%, and a moisture uptake of less than 10%. Also provided are composition consisting essentially of a cationic polyurethane; a neutralizer; and an oil, wherein the cationic polyurethane has a Young's modulus above 150 MPa; an elongation at break from about 15% to about 300%; and a moisture uptake of less than 10%.

In some aspects, the cationic polyurethane in the provided compositions is a salt of the formula: [W, V, Y and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; X is a neutralizing ion; the molecular weight of W is about 1,000 g/mol; the molar ratio of V:W is 1:0.18 to about 1:0.32; the molar ratio of V:Y is 1:0.24 to about 1:0.72; and the molar ratio of V:Z is 1:0.08 to about 1:0.47. In one alternative, the cationic polyurethane in the provided compositions is a salt of the formula: [W, V, Y and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; X is a neutralizing ion; the molecular weight of W is about 2,000 g/mol; the molar ratio of V:W is 1:0.08 to about 1:0.18; the molar ratio of V:Y is 1:0.36 to about 1:0.82; and the molar ratio of V:Z is 1:0.08 to about 1:0.49. In another alternative, the cationic polyurethane in the provided compositions is a salt of the formula: [W, V, Y and Z]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; X is a neutralizing ion; the molecular weight of W is about 3,000 g/mol; the molar ratio of V:W is 1:0.05 to about 1:0.13; the molar ratio of V:Y is 1:0.4 to about 1:0.85; and the molar ratio of V:Z is 1:0.08 to about 1:0.49.

In one alternative the cationic polyurethane is a salt of the formula: [W, V, Y, Z, and $Z^1$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^1$ is the product formed from ethoxylated polyol monomer; X is a neutralizing ion; the molecular weight of W is about 1,000 g/mol; the molar ratio of V:W is 1:0.19 to about 1:0.33; the molar ratio of V:Y is 1:0.19 to about 1:0.7; the molar ratio of V:Z is 1:0.08 to about 1:0.49; and the molar ratio of V:$Z^1$ is 1:0 to about 1:0.03. In another alternative, the cationic polyurethane in the provided compositions is a salt of the formula: [W, V, Y, Z, and $Z^1$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^1$ is the product formed from ethoxylated polyol monomer; X is a neutralizing ion; the molecular weight of W is about 2,000 g/mol; the molar ratio of V:W is 1:0.09 to about 1:0.18; the molar ratio of V:Y is 1:0.31 to about 1:0.8; the molar ratio of V:Z is 1:0.09 to about 1:0.51; and the molar ratio of V:$Z^1$ is 1:0 to about 1:0.03. In another alternative, the cationic polyurethane in the provided compositions is a salt of the formula: [W, V, Y, Z, and $Z^1$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^1$ is the product formed from ethoxylated polyol monomer; X is a neutralizing ion; the molecular weight of W is about 3,000 g/mol; the molar ratio of V:W is 1:0.05 to about 1:0.13; the molar ratio of V:Y is 1:0.36 to about 1:0.83; the molar ratio of V:Z is 1:0.09 to about 1:0.52; and the molar ratio of V:$Z^1$ is 1:0 to about 1:0.03. In another alternative, the cationic polyurethane in the provided compositions is a salt of the formula: [W, V, Y, Z, and $Z^2$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^2$ is the product formed from hydroxylated alkyl acid monomer; X is a neutralizing ion; the molecular weight of W is about 1,000 g/mol the molar ratio of V:W is 1:0.19 to about 1:0.33; the molar ratio of V:Y is 1:0.14 to about 1:0.44; the molar ratio of V:Z is 1:0.08 to about 1:0.47; and the molar ratio of V:$Z^2$ is 1:0.05 to about 1:0.33. In another alternative, the cationic polyurethane in the provided compositions is a salt of the formula: [W, V, Y, Z, and $Z^2$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^2$ is the product formed from hydroxylated alkyl acid monomer; X is a neutralizing ion; the molecular weight of W is about 2,000 g/mol; the molar ratio of V:W is 1:0.09 to about 1:0.18; the molar ratio of V:Y is 1:0.26 to about 1:0.53; the molar ratio of V:Z is 1:0.09 to about 1:0.49; and the molar ratio of V:$Z^2$ is 1:0.05 to about 1:0.35. In another alternative, the cationic polyurethane in the provided compositions is a salt of the formula: [W, V, Y, Z, and $Z^2$]X$^-$, wherein W is the product formed from polycarbonate polyol monomer; V is the product formed from polyisocyanate monomer; Y is the product formed from $C_{1-8}$alkyldiol monomer; Z is the product formed from $C_{1-8}$aminoalkyldiol monomer; $Z^2$ is the product formed from hydroxylated alkyl acid monomer; X is a neutralizing ion; and the molecular weight of W is about 3,000 g/mol; the molar ratio of V:W is 1:0.05 to about 1:0.13; the molar ratio of V:Y is 1:0.3 to about 1:0.56; the molar ratio of V:Z is 1:0.09 to about 1:0.5; and the molar ratio of V:$Z^2$ is 1:0.05 to about 1:0.35.

In yet another alternative, V is the product formed from isophorone diisocyanate monomer; Y is the product formed from 1,4-butanediol monomer; and Z is the product formed from 3-(dimethylamino)-1,2-propanediol monomer. In yet another alternative, the cationic polyurethane is a salt of the formula:

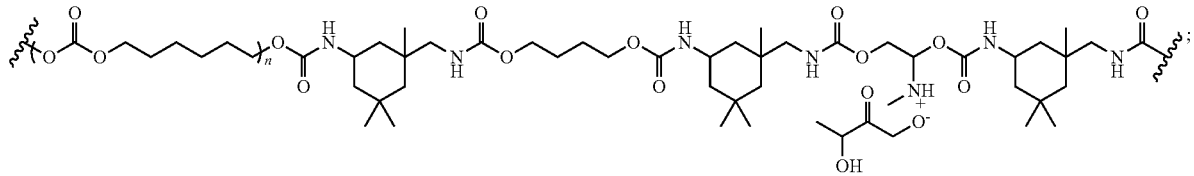

-continued

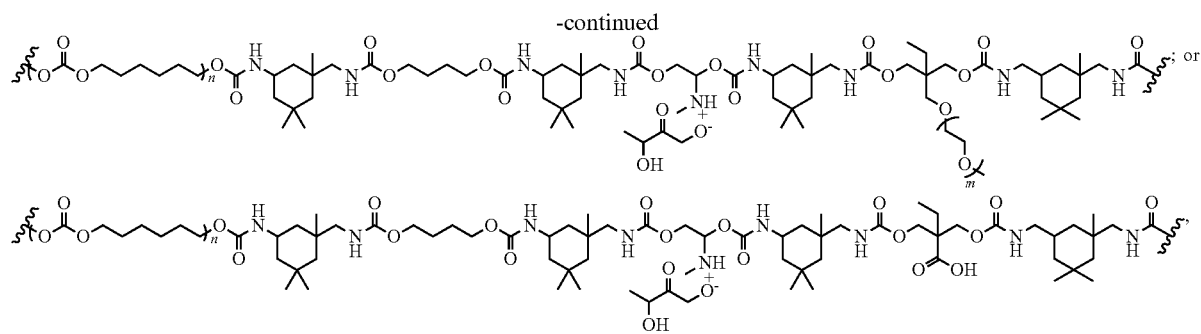

wherein n is 6 to 21 and m is 19 to 31.

In some aspects, the cationic polyurethane in the provided compositions is selected from PU-363, PU-399, PU-400, PU-377, PU-404, PU-378, PU-383, PU-398, PU-401, PU-402, PU-403, PU-385, PU-376, PU-408, PU-409, PU-396, PU-413, PU-414, PU-362, and PU-372. In another aspect, the cationic polyurethane is selected from PU-362, PU-376, PU-377, PU-378, and PU-404. In yet another aspect, the cationic polyurethane is selected from PU-363, PU-377, and PU-378.

Also provided is a hair treatment composition comprising a cationic polyurethane having the formula:

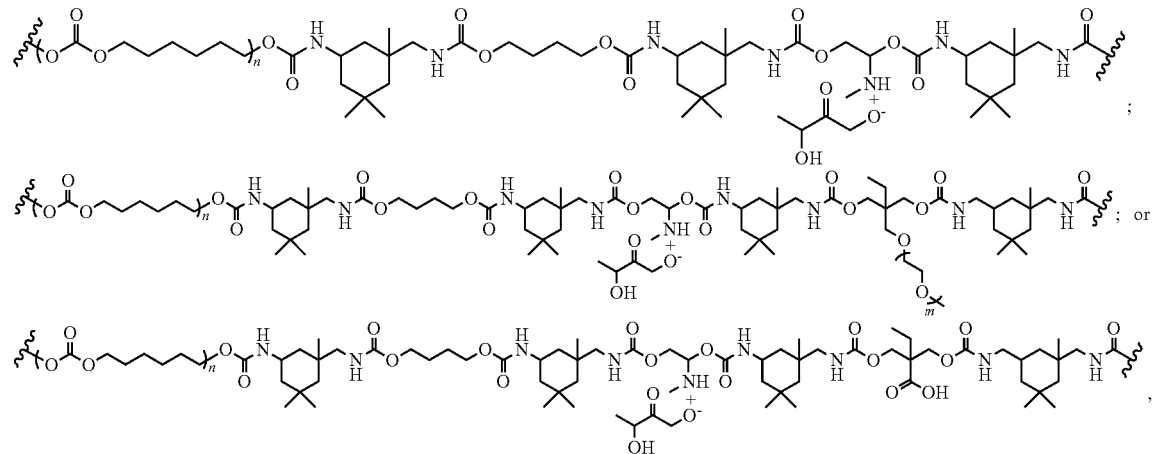

wherein n is 6 to 21 and m is 19 to 31.

Further provided is a hair treatment composition consisting essentially of a cationic polyurethane having the formula:

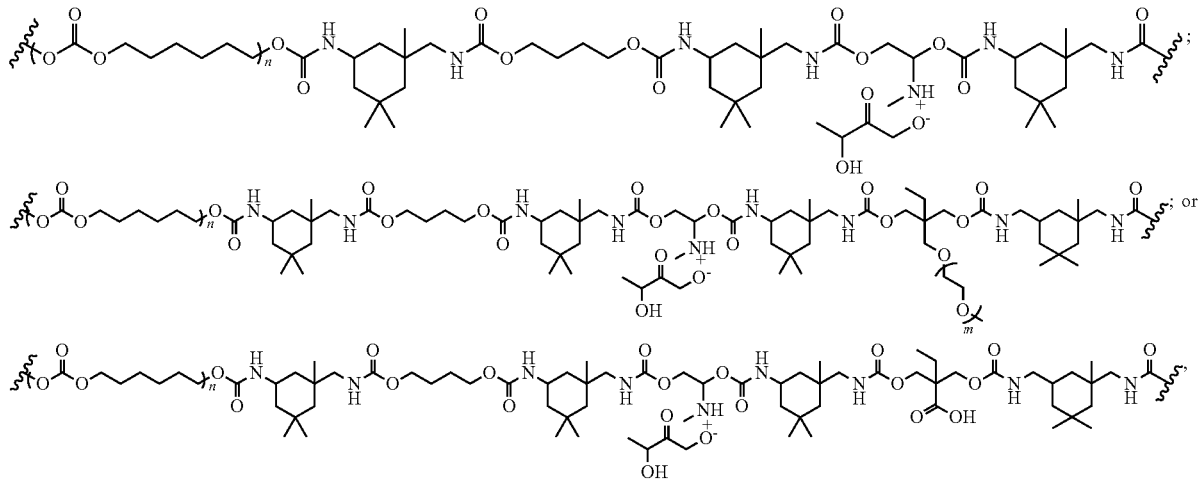

wherein n is 6 to 21 and m is 19 to 31; a neutralizer; and an oil.

In some aspects, the cationic polyurethane is dispersed in water.

In some aspects, the cationic polyurethane is in the form of a particle.

In some aspects, the cationic polyurethane comprises uniform particles having an average particle diameter of about 20 to about 80 nm.

In some aspects, the cationic polyurethane comprises bimodal or multimodal particles having an average particle diameter of about 100 to about 300 nm.

In some aspects, the cationic polyurethane is present in an amount of 25% to 35% based on the total weight of the composition.

In some aspects, the compositions described herein further comprise a neutralizer. The neutralizer may be e.g., an acid neutralizer such as lactic acid. In some aspects, the neutralizer:$C_{1-8}$aminoalkyldiol monomer ratio is from about 0.8 to about 1.2.

In some aspects, the compositions described herein further comprise an oil. Oils for use in the disclosed compositions can be selected from mineral, animal, plant or synthetic oils. In one aspect, the oil is linoleic acid or a mixture of fatty acids. Examples include, but are not limited to fragrance oils, emollients, monoterpenoids, fatty alcohols, fatty acids, fatty esters, fatty ethers, fluorinated small molecules (e.g., perfluoromethylcyclopentane, perfluoroperhydrophenanthrene, perfluoro-1,3-dimethylcyclohexane, perfluoromethyldecalin, and perfluoroperhydrobenzyltetralin), and mixtures thereof. In another aspect, the oil is present in an amount ranging from about 0.2 to about 1.65% based on the total weight of the composition. In another aspect, the oil is present in an amount of about 0.2 to about 0.25% based on the total weight of the composition.

In one aspect, the disclosed compositions are applied to the hair with water.

In one aspect, the disclosed compositions, when applied to the hair, change the texture and appearance.

In one aspect, the disclosed compositions, when applied to the hair, improve hold, i.e., hair that is formed into a given curl or style retains that curl or style over time.

In one aspect, the disclosed compositions, when applied to the hair, provide sufficient stylability, i.e., the composition applied to hair supplies sufficient rigidity and flexibility to form and maintain a style.

In one aspect, the disclosed compositions, when applied to the hair, minimize flyaways, i.e., there are minimal individual hair fibers that do not conform to the given curl or style.

In one aspect, the disclosed compositions, when applied to the hair, preserves curl shape, i.e., hair that is formed into a given curl retains that curl over time.

In one aspect, the disclosed compositions, when applied to the hair, provides natural curl enhancement, i.e., hair that naturally tends to curl displays a more defined and less diffused curl pattern.

The compositions described herein may further comprise an antioxidant. Antioxidants that may be suitable with the compositions described herein include, but are not limited to, acai oil, alpha lipoic acid, green and white tea, retinol, vitamin C, Vitamin E, butylated hydroxytoluene, butylated hydroxyanisole, coenzyme Q10 (Co Q-10), isoflavones, polyphenols, curcumin, turmeric, pomegranate, rosemary, glutathione, selenium, and zinc.

4. Methods of Use

The compositions described herein may be used for any cosmetic application. Such applications include, but are not limited to, skin-care creams, eye and facial makeup (e.g., mascara, eye liner, eyebrow makeup, and the like), deodorants, lotions, powders, perfumes, baby products, body butters; and hair products (e.g., permanent chemicals, hair colors, hair sprays, and gels).

In one aspect, the compositions described herein are used as a hair product, e.g., in a conventional manner for providing hairstyle/hold benefits.

In an exemplary aspect, an effective amount of a composition described herein may be sprayed or applied onto dry or damp hair before and/or after the hair is styled. As used herein "effective amount" means an amount sufficient to provide the hair hold and style performance desired according to the length and texture of the hair.

In one aspect, the present disclosure provides a method of fixing hair comprising the step of applying a polyurethane disclosed herein. In one aspect, the present disclosure provides a method of retaining the curl of hair comprising the step of applying polyurethane disclosed herein.

In one aspect, the present disclosure also includes a method to determine the curl retention of a hair tress. In one aspect, the method of measuring the curl retention of a hair tress includes the steps of a) measuring the length of the hair tress; b) applying a composition comprising a waterborne polyurethane disclosed herein to the hair tress; c) blow drying the hair tress for 90 seconds without brushing; d) curling the hair tress with a ¾ inch curling rod at 370° F. for 10 seconds; e) mechanically manipulating the hair tress by pulling, combing and brushing; f) measuring the length of the curled hair tress.

In one aspect, the method of measuring the curl retention of a hair tress, includes the steps of a) measuring the length of the hair tress; b) applying the composition comprising a waterborne polyurethane disclosed herein to the hair tress; c) blow drying the hair tress for 90 seconds without brushing; d) curling the hair tress with a ¾ inch curling rod at 370° F. for 10 seconds; e) subjecting the hair tress to humidity; f) measuring the length of the curled hair tress. In one aspect, the curled hair tress is subjected to 60%, 70%, 75%, 80% or 90% relative humidity for 3, 5, 10, 15, 20, 25, 30, 35, 40, 45, 50, 55, 60, 75, 90, 105, 120, 180 or 210 minutes at a temperature of 25° C.

In one aspect, the method of measuring the curl retention of a hair tress, includes the steps of a) measuring the length of the hair tress; b) applying the composition comprising a waterborne polyurethane disclosed herein to the hair tress; c) blow drying the hair tress for 90 seconds without brushing; d) curling the hair tress with a ¾ inch curling rod at 370° F. for 10 seconds; e) subjecting the hair tress to humidity; f) brushing the hair tress; g) measuring the length of the curled hair tress. In a particular aspect, the curled hair tress is subjected to 60%, 70%, 75%, 80% or 90% relative humidity for 2, 4, 8, 16, 32, or 48 hours at a temperature of 25° C. and brushed 1, 3, 5, 8, 10, 13, 15, or 20 times.

In one aspect, the method of evaluating the curl retention of a hair tress, includes the steps of a) applying the composition comprising a polyurethane disclosed herein to the hair tress; b) blow drying the hair tress for 90 seconds without brushing; c) blinding the prepared hair tress; d) evaluating the sensory properties of the tress in a blinded fashion. In one aspect, the prepared tress is graded on a scale of −2 to 2 for natural feeling and overall sensory attributes.

In one aspect, the cationic polymers described herein are for use in a conditioner or leave-in-conditioner.

In one aspect, provided is a method for styling hair comprising a) applying a cationic polyurethane-based composition described herein (the so-called "first wave"; b)

heating the hair to a temperature sufficient to induce curl; and c) applying an anionic polyurethane having a Young's modulus above 150 MPa, an elongation at break from about 15% to about 300%, and a moisture uptake of less than 10% (the so-called "second wave"). In one aspect, steps a), b), and c) are repeated.

EXEMPLIFICATION

Example 1. Chemical Compositions of Cationic Waterborne Polyurethane

Cationic waterborne polyurethanes were synthesized primarily using polycarbonate diol, 1,4-butanediol (BD), isophorone diisocyanate (IPDI), and 3-(dimethylamino)-1,2-propanediol (DMAPD); selectively, the nonionic chain extenders Tegomer D3403 (ethoxylated polyether-1,3-diol) and 2,2-bis(hydroxymethyl)butyric acid (DMBA) were incorporated in cationic waterborne polyurethanes respectively to achieve desired physical properties. A mild acid, lactic acid, was used as a neutralizer. For each monomer, the molar ratio to NCO is listed in Table 1. Moreover, a beneficial oil could be also incorporated into cationic waterborne polyurethanes to provide improved sensory attributes.

TABLE 1

| PU Name | NCO | Polyol (molar ratio to NCO) | Other diol segment (molar ratio to NCO) | Ionic chain extender (molar ratio to NCO) | Nonionic chain extender (molar ratio to NCO) | Neut. | Degree of Neut. | Oil |
|---|---|---|---|---|---|---|---|---|
| 363 | IPDI | PCD1K_0.29 | BD_0.27 | DMAPD_0.45 | N/A | Lactic acid | 100% | N/A |
| 399 | IPDI | PCD1K_0.29 | BD_0.26 | DMAPD_0.44 | N/A | Lactic acid | 100% | N/A |
| 400 | IPDI | PCD1K_0.20 | BD_0.42 | DMAPD_0.38 | N/A | Lactic acid | 100% | N/A |
| 377 | IPDI | PCD1K_0.28 | BD_0.42 | DMAPD_0.30 | N/A | Lactic acid | 100% | N/A |
| 404 | IPDI | PCD1K_0.29 | BD_0.41 | DMAPD_0.30 | N/A | Lactic acid | 100% | N/A |
| 378 | IPDI | PCD1K_0.28 | BD_0.51 | DMAPD_0.21 | N/A | Lactic acid | 100% | N/A |
| 383 | IPDI | PCD1K_0.28 | BD_0.61 | DMAPD_0.12 | N/A | Lactic acid | 100% | N/A |
| 398 | IPDI | PCD1K_0.29 | BD_0.58 | DMAPD_0.12 | Tegomer_0.0049 | Lactic acid | 100% | N/A |
| 401 | IPDI | PCD1K_0.29 | BD_0.60 | DMAPD_0.12 | N/A | Lactic acid | 100% | N/A |
| 402 | IPDI | PCD3K_0.10 | BD_0.78 | DMAPD_0.12 | N/A | Lactic acid | 100% | N/A |
| 403 | IPDI | PCD1K_0.30 | BD_0.26 | DMAPD_0.44 | N/A | Lactic acid | 80% | N/A |
| 385 | IPDI | PCD1K_0.28 | BD_0.61 | DMAPD_0.12 | N/A | Lactic acid | 110% | N/A |
| 376 | IPDI | PCD1K_0.29 | BD_0.27 | DMAPD_0.45 | N/A | Lactic acid | 100% | Linoleic acid |
| 408 | IPDI | PCD1K_0.28 | BD_0.42 | DMAPD_0.30 | N/A | Lactic acid | 100% | Linoleic acid |
| 409 | IPDI | PCD1K_0.28 | BD_0.42 | DMAPD_0.30 | N/A | Lactic acid | 100% | Mixture of FAs |
| 396 | IPDI | PCD1K_0.28 | BD_0.61 | DMAPD_0.12 | N/A | Lactic acid | 100% | Linoleic acid |
| 413 | IPDI | PCD1K_0.20 | BD_0.56 | DMAPD_0.25 | N/A | Lactic acid | 100% | N/A |
| 414 | IPDI | PCD1K_0.29 | BD_0.56 | DMAPD_0.16 | N/A | Lactic acid | 100% | N/A |
| 355 | IPDI | PCD1K_0.29 | BD_0.27 | DMBA_0.22 | DMAPD_0.22 | Na$_2$CO$_3$ | 100% | N/A |
| 362 | IPDI | PCD1K_0.29 | BD_0.27 | DMAPD_0.22 | DMBA_0.22 | Lactic acid | 100% | N/A |
| 372 | IPDI | PCD1K_0.29 | BD_0.27 | DMAPD_0.22 | DMBA_0.22 | Lactic acid | 100% | Linoleic acid |

PCD1K = polycarbonate diol with molecular weight at 1,000 g/mol; PCD3K = polycarbonate diol with molecular weight at 3,000 g/mol.

Overall, inventive cationic waterborne polyurethanes possessed optimal physical properties as defined herein: (1) Young's modulus >150 MPa, (2) Elongation at break between 15% and 300%, and (3) Water uptake (a) below 10% for WBPUs without additive (b) below 8% for WBPUs with additive. See Table 2.

TABLE 2

| PU Name | Young's Modulus (MPa) | Elongation at break (%) | Water Uptake (%) |
|---|---|---|---|
| 363 | 218 ± 21 | 292 ± 21 | 8.01 ± 0.20 |
| 399 | 268 ± 10 | 255 ± 43 | 7.72 ± 0.26 |
| 400 | 326 ± 2 | 24 ± 23 | 7.55 ± 0.40 |
| 377 | 253 ± 10 | 95 ± 10 | 5.23 ± 0.40 |
| 404 | 173 ± 22 | 253 ± 41 | 5.27 ± 0.37 |
| 378 | 228 ± 15 | 163 ± 22 | 3.26 ± 0.33 |
| 383 | 198 ± 12 | 172 ± 48 | 2.46 ± 0.16 |
| 398 | 145 ± 11 | 242 ± 10 | 2.86 ± 0.25 |
| 402 | 170 ± 7 | 47 ± 7 | 1.51 ± 0.17 |
| 376 | 266 ± 12 | 307 ± 25 | 7.51 ± 0.21 |
| 355 | 318 ± 24 | 62 ± 21 | 5.91 ± 0.47 |
| 362 | 295 ± 10 | 170 ± 41 | 2.88 ± 0.93 |
| 372 | 319 ± 42 | 150 ± 45 | 2.87 ± 0.56 |
| 413 | 340 | 10 | 6.22 ± 0.08 |
| 414 | 146 ± 12 | 216 ± 6 | 3.61 ± 0.11 |

Particle size and distribution of cationic waterborne polyurethanes can be divided by two types. Depending on chemical compositions, one type of cationic waterborne polyurethanes showed uniform particle size distribution and average particle diameter was in the range of about 20 to about 80 nm. The other type of cationic waterborne polyurethane showed large particle size and bimodal/multimodal particle size distribution as indicated by average particle sizes in the range of 100 to approximately 300 nm and large standard deviation of particle size. See Table 3.

TABLE 3

| PU Name | Particle Size (TEM, nm) |
|---|---|
| 363 | 29.8 ± 3.9 |
| 399 | 29.9 ± 4.3 |
| 400 | 29.6 ± 5.0 |
| 377 | 34.1 ± 7.5 |
| 378 | 36.6 ± 10.7 |
| 383 | 150.3 ± 112.9 |
| 398 | 111.2 ± 45.4 |
| 402 | 139.6 ± 50.6 |
| 376 | 21.3 ± 4.5 |
| 355 | 41.3 ± 18.3 |
| 362 | 57.0 ± 15.6 |
| 372 | 79.7 ± 29.7 |

TABLE 3-continued

| PU Name | Particle Size (TEM, nm) |
|---|---|
| 413 | 60.1 ± 16.7 |
| 414 | 106.2 ± 25.2 |

Example 2. Mechanical Performance

The Young's modulus is a measure of the ability of a material to withstand changes in length when under uniaxial tension or compression. A higher Young's modulus typically indicates that the material is more rigid. The elongation at break, also known as fracture strain, is the ratio between changed length and initial length after breakage of the test specimen. A higher elongation at break expresses the capability of a material to resist fracture. For a composition applied to hair to hold the shape of the hair, the Young's modulus and elongation at break of the composition should be such that the composition provides rigidity to the hair but is not brittle.

A comparison of Young's modulus and the elongation at break for the some of the polyurethanes disclosed herein was made to several commercially available polyurethane products. The Young's modulus and the elongation at break can be determined by a protocol defined to measure mechanical properties is developed in compliance with ASTM D638, ASTM D412, test guidelines. In particular, the following protocol can be used to determine the Young's modulus and elongation at break (or ultimate elongation) of dry film of polyurethanes. Testing requires approximately 10-20 min per sample to complete.

Materials:
>25 g polyurethane aqueous dispersion
1 clean rectangular mold (2 mm×20 mm×45 mm) grooved on Teflon sheet per sample
1 clean razor blade
Scotch tape
Universal Testing Machine mounted with extension grip geometry Sample Preparation:
1. Prepare 25 g of 10 wt % WBPU solution from their respective stock solution.
2. Apply 2.5 mL prepared solution in each mold (2 mm×20 mm×45 mm) and allow drying for 2 days to give WBPU film.
3. After it dries out, use a spatula to remove film from the mold.
4. Use the razor blade to cut corners and get film with around 15 mm width and around 150-300 micron thickness. Make sure that the film is free of air bubbles.
5. Label the test film.
6. Cut four pieces of tape (20 mm) per sample and adhere them to both sides of the specimen strip and make a dog-bone shaped sample to improve hold of sample in grip. Store the prepared test films in desiccators for 1-2 hour to fully dry them. Take one sample out of desiccators at a time for testing.

Sample Testing
1. Balance the load registering on the universal testing machine so that it reads 0 Newtons.
2. Use calipers to set a distance of 20 mm between the top and bottom extension grip geometries.
3. Mount a sample in the extension grips and secure tightly, ensuring that the scotch tape is not visible, and that the sample is as close to vertical as possible in both vertical planes.
4. Stretch the sample slightly, by separating the geometries until a force of 2-5 N is registered.
5. Begin a tensile testing run on the universal testing machine at a speed of 100 mm/minute, stopping the test upon sample fracture.
6. Elongation at break is calculated at the elongation at which the material fractures.
7. Young's modulus is calculated as the modulus during the initial, elastic portion of deformation by calculating the slope of a linear fit to that region with an R value >0.99.
a) low modulus and high elongation (Avalure UR 450, C1004, Polyderm PE/PA ED, Polyderm PE/PA), which leads to inferior curl hold (e.g., hold is temporary, transient, or short-lived) or
b) high modulus and low elongation (DynamX, DynamX/ $H_2O$, Luviset PUR), which leads to a brittle material with low performance (e.g., resin is brittle or fractures) after manipulation.

Example 3. Hydrophobicity/Water Uptake of Polyurethane

The moisture uptake properties, under highly humid environment, of WBPU dry films have been linked to their long lasting hold performance. As such, it is important to be able to reproducibly and accurately evaluate such moisture uptake properties to enable predictive in vitro and in vivo evaluation of WBPU dry films. The following protocol can be used to determine moisture uptake ability of WBPU dry films under high humid environment. Test requires about 2-3 days per sample set to complete Materials
>15 g WBPU solution
1 clean cell culture petri dish (60 mm dia×15 mm H) per sample
Humidity chamber with flexibility to control temperature and relative humidity (RH)

Sample Testing
1. Prepare 15 g of 10 wt % WBPU solution from their respective stock solution.
2. Label cell culture petri dishes for each sample and measure their empty weight ($W_{pd}$).
3. Apply 4 mL prepared solution in each petri dish (3 samples per WBPU and allow to equilibrate for 20 hours at 25° C. and 50% RH in humidity chamber.
4. After equilibration, measure and record sample weight (Wi).
5. Place the samples to humidity chamber at 25° C. and 90% RH and allow equilibration to high humidity for 20 hours.
6. Measure and record final sample weight (W).

Sample Analysis
Calculate % moisture uptake using the following equation:

$$\% \text{ moisture uptake} = \left[ \frac{((Wf - Wpd) - (Wi - Wpd))}{(Wi - Wpd)} \right] \times 100\%$$

Example 4. Two Wave Styling

Since the isoelectric point (IEP, the pH at which a molecule or a substance carries no net electrical charge) of hair is about 3.67 (see Chemical and Physical Behavior of Human Hair, 5$^{th}$ ed.; p 388), the surface of hair bears a net negative charge at pHs above its IEP, where most hair care products are formulated. Anionic WBPUs which are often used in different hair care products, are therefore more likely to bind to hair surfaces by polar and Van der Waals interactions (see Chemical and Physical Behavior of Human Hair). By contrast, cationic WBPUs that carry opposite charges such as those described herein can bind to hair surfaces through the formation of ionic bonds. To achieve more enhanced performance, a new two-wave styling technology was developed, in which cationic and anionic WBPUs are used together to create synergistic styling properties. The detailed mechanism is shown in FIG. 1. Hair surface naturally bears a net negative charge. Therefore cationic WBPUs, when applied as the first layer, are readily attracted to hair surface, providing strong hold to hair and creating the so-called a first wave styling. To take advantage of the excess positive charges of the cationic WBPU particles, a second layer of anionic WBPU particles is then deposited. The ionic interaction between the cationic and anionic WBPUs further enhances the hold and provides a second wave of styling.

Tress Testing

To test the two-wave styling concept, systematic in vitro testing of cationic and anionic WBPUs was conducted. In all in vitro testing, a cationic WBPU was applied to a tress as an aqueous dispersion at 3 wt % polymer, and then an anionic WBPU was applied as an aqueous dispersions at 3 wt % polymer. The tress was blow dried for 90 seconds, then curled using ¾" curling rod at 370° F. for 10 seconds and cooled in coiled formation. The tress was then subjected to 75% relative humidity at 25° C. for 15 minutes and then mechanically stressed by extending the tress to its original length, holding for 1 second, and releasing. Results show that both excellent high humidity curl retention and good sensory properties could be achieved.

As a preliminary screening, cationic and anionic WBPUs that were applied either in the first or second wave were tested alone. Results showed that cationic WBPU PU 363 showed better curl length and curl shape retention after high humidity. This was attributed to the strong ionic interactions between the WBPU, which has a relatively high cationic charge density, and inherently anionic hair surfaces. Further screening of all cationic WBPUs of different cationic charge densities showed that cationic WBPUs with higher charge densities provide better high heat curl retention (PU 363, PU 377, and PU 378).

Figure 2A:
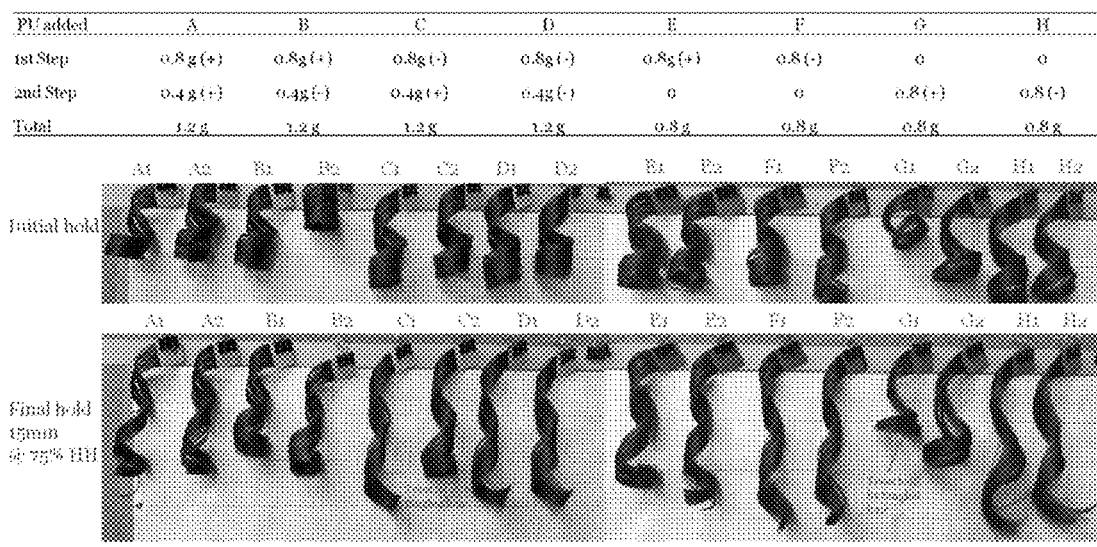
FIG. 2a shows an example of hair tresses before and after high humidity test styled using two-wave cationic/anionic application described herein.
Figure 2B:
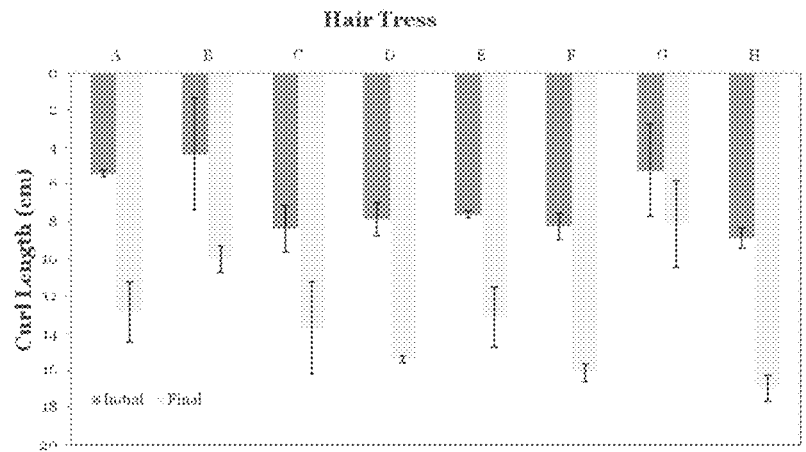
FIG. 2b shows the lengths of curls measured before and after high humidity testing for tresses treated either with two-wave styling with cationic and anionic WBPUs vs. one-wave application of either cationic or anionic WBPUs. The best initial hold and the best curl retention after high humidity was observed in set B (two-wave styling; cationic WBPU followed by anionic WBPU; (+)/(−)) as opposed to the tresses styled using (+) or (−) WBPUs alone or in the opposite order ((−)/(+)).

When applied in a two-wave process where a cationic WBPU is first applied to the hair tress, a curl is styled, followed by the application of spray carrying an anionic WBPU; excellent high humidity curl retention was achieved. FIG. 2a shows an example of hair tresses before and after high humidity test styled using two-wave cationic/anionic WBPU application as described above. Set B, where 0.8 g of the cationic WBPU PU 363 was applied initially at a 3 wt % polymer concentration followed by 0.4 g of anionic WBPU, also at 3 wt % solid polymer concentration, showed the best initial hold and curl retention after high humidity as opposed to the tresses styled using cationic (+) alone or anionic (−) alone WBPUs only or anionic followed by cationic ((−)/(+)) WBPU application (FIG. 2b). This supports two-wave styling concept where at first strong ionic interactions are formed between anionic hair surfaces and cationic WBPU dispersions followed by additional ionic interactions of cationic WBPU dispersions with anionic WBPU dispersions creating long-lasting curl style.

Mannequin Testing

Figure 3:
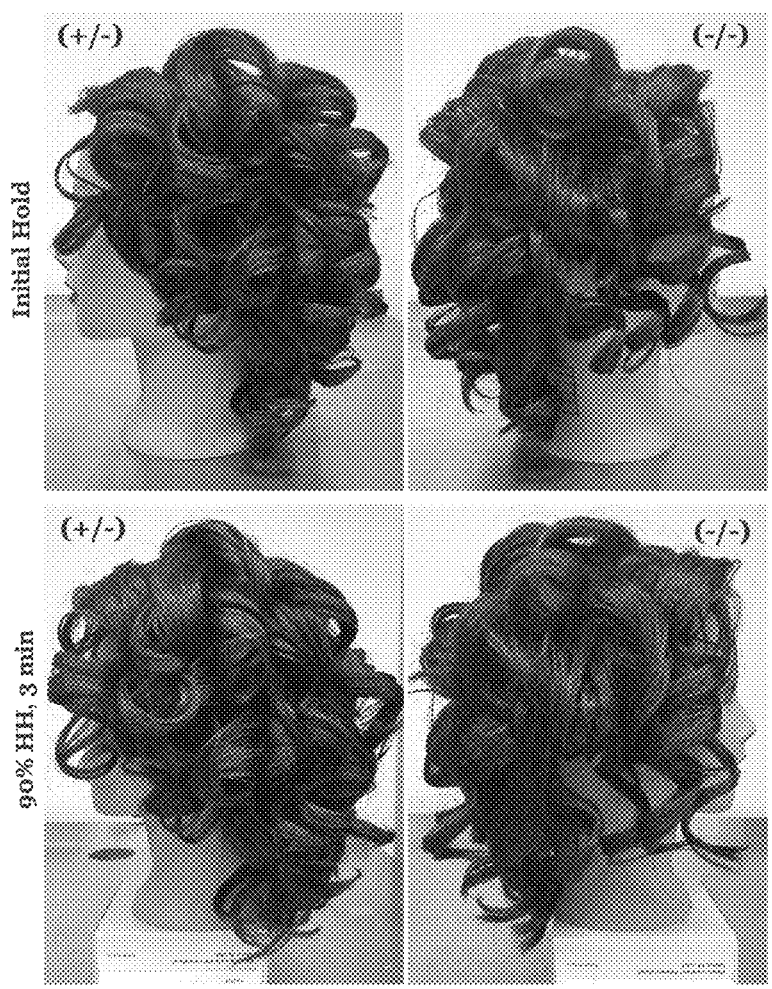
FIG. 3 shows the results of mannequin testing using aqueous dispersions of cationic polyurethanes using the two-wave method described herein. The two-wave styling (+/−) was applied on the left side using a representative cationic WBPU PU 377 as the first wave and anionic WBPU as the second wave, showing better curl hold, curl shape, and curl definition compared to the application on the right side of anionic WBPU in both waves (−/−). A blinded, trained sensory evaluator determined that the curls generated using the (+/−) two-wave treatment was aesthetically preferable to the curls generated using the (−/−) treatment.
Figure 4:
FIG. 4 shows the results of mannequin testing using cationic polyurethanes in different styling formulations using the two-wave method described herein. The two-wave styling (+/−) applied on the right side of the mannequin head showed better initial curl hold, curl shape, and better curl retention after humidity testing than the application on the left where a control formulation as the first wave and anionic WBPU as the second wave (Ctrl/−) was used. The curls made with the (Ctrl/−) treatment fell significantly compared to the two-wave (+/−) treatment. A blinded, trained sensory evaluator determined that the style obtained using the (+/−) two-wave treatment was aesthetically preferable to the style obtained using the (Ctrl/−) treatment.

In addition to the testing on hair tresses, extensive mannequin testing was conducted to evaluate the hold, sensory properties, and visual effects of the cationic polyurethanes. Both cationic and anionic WBPUs can be applied as either aqueous dispersions (FIG. 3) or in different styling formulations (FIG. 4). The results in FIG. 3 and FIG. 4 show that two-wave styling (cationic followed by anionic (+/−)) led to superior performance (better hold and high humidity curl retention). Performance using only anionic WBPU dispersions in both waves is shown by (−/−). All dispersions were applied at a 3 wt % WBPU concentration. The two-wave styling (+/−) was carried out using a representative cationic PU 377, and anionic WBPU dispersions as the second wave. Anionic dispersions that can be used are found in PCT/US2017/021025. In FIG. 4, the two-wave styling (+/−) was carried out using NoFrizz Conditioner (available from Living Proof, Cambridge Mass.) containing a cationic WBPU (PU 377) as the first wave and an anionic WBPU dispersion as the second wave, and showed better performance compared to using the control NoFrizz conditioner as the first wave and anionic WBPU as the second wave (Ctrl/−).

In Vivo Performance

Figure 5:
FIG. 5 shows in vivo testing showing better initial hold and high humidity curl retention using aqueous dispersions of cationic polyurethanes by two-wave styling described herein. Curls on the left side of the panelist head showed better curl retention after humidity test with (+/−) two-wave styling application, while curls on the right side of the panelist head lost their shape and fell more loosely where the (−/−) application was performed. A blinded, trained sensory evaluator determined that the curls generated using the (+/−) two-wave treatment were aesthetically preferable to the curls generated using the (−/−) treatment.

To validate the in vitro results, and to assess performance under normal hair care product use conditions, cationic and anionic WBPUs were applied as either 3 wt % aqueous dispersions or in different styling formulations. Although performance differences are less pronounced when compared with highly controlled in vitro testing, two-wave styling did consistently show improved performance compared to other styling methods, e.g., only anionic WBPU in both waves, in achieving strong hold and high humidity curl retention. See FIG. 5. The two-wave styling (cationic followed by anionic (+/−)) was carried out using the cationic WBPU dispersion PU 377, as the first wave and the anionic WBPU dispersion as the second wave, which showed better performance compared to using only the anionic WBPU dispersions in both waves (−/−). All dispersions were applied at a 3 wt % WBPU concentration.

Figure 6:
FIG. 6 shows in vivo testing showing better natural curl definition using cationic polyurethanes in different styling formulations by two-wave styling described herein. Natural curls of the panelist are enhanced and appear less frizzy on the left side where (+/−) two-wave styling was applied, while curls on the right side of the panelist appear less defined and less desirable where a control formulation only was applied. A blinded, trained sensory evaluator determined that the style obtained with the (+/−) two-wave treatment was aesthetically preferable to the style obtained with the control treatment.

When the cationic and the anionic WBPUs were incorporated into NoFrizz Conditioner or Curl Defining Styling Cream (available from Living Proof, Cambridge Mass.), respectively, the two-wave styling provided much better natural curl definition compared to the current formulations. See FIG. 6. The two-wave styling (+/−) was carried out using NoFrizz Conditioner containing a cationic WBPU (PU 377) as the first wave and Curl Defining Styling Cream containing an anionic WBPU as the second wave, and showed much better curl definition compared to using NoFrizz Conditioner as the first wave and Curl Defining Styling Cream as the second wave (Ctrl).

Example 5. Showering Conditioner

In order to create a long-lasting hairstyle, a consumer must typically expend additional time and energy applying dedicated styling products to their hair after shampooing and conditioning. For many consumers, spending the time to apply these additional styling products is not feasible or desirable. Thus, there is a need in the market for more user-friendly, time-saving styling products. The cationic polyurethanes described herein can be leveraged to address this problem.

Hair conditioners are typically low pH (<7) formulations containing smoothening and conditioning molecules functionalized with positively charged quaternium functional groups, and are therefore incompatible with traditional anionic styling polymers used widely in the industry. However, when the cationic polyurethanes described herein are formulated in conditioners or leave-in-conditioners, the formulations were found to provide excellent style hold in addition to smoothing and conditioning. See e.g., FIG. 7 and FIG. 8.

Table 4 shows an exemplary list of conditioners and leave-in-conditioners comprising the disclosed cationic polyurethanes.

TABLE 4

| Cationic WBPU Incorporated | Wt % WBPU | Type of Formulation |
|---|---|---|
| 363 | 5 | Conditioner |
| 362 | 5 | Conditioner |
| 376 | 5 | Conditioner |
| 377 | 5 | Conditioner |
| 378 | 5 | Conditioner |
| 377 | 10 | Conditioner |
| 377 | 5 | Leave-In Conditioner |
| 404 | 10 | Conditioner |

Figure 7:
FIG. 7 shows an example of the curls generated using a hot curling iron, on hair washed with conditioner containing 5% cationic polyurethane (left) or with the same conditioner without a cationic polyurethane. The curl hold is significantly better on the left side of the panelist where the formulation with cationic polyurethane was applied—the curls have better definition, shape and bounce. Curls are limper and looser on the right side where conditioner base alone was applied. A blinded, trained sensory evaluator determined that the curls generated using conditioner containing cationic WBPU was aesthetically preferable to the curls generated using the conditioner alone.
Figure 7:
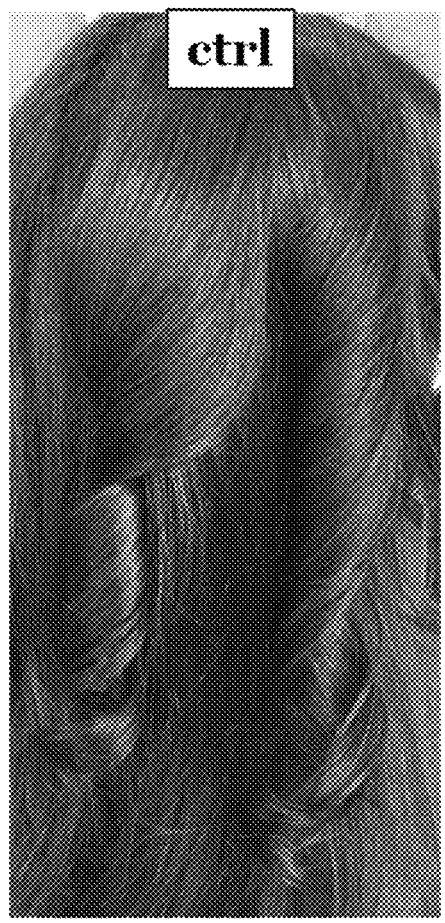

When conditioners containing the disclosed cationic polyurethanes are used in place of conditioners without the cationic polyurethanes, curl hold was significantly improved. FIG. 7 shows an example of the curls generated using a hot curling iron after washing with either conditioner containing 5% cationic polyurethane PU 363 (left) or with the same conditioner base without a cationic polyurethane. Because the cationic polyurethane styling polymer can be formulated directly into the conditioner, the consumer can achieve long-lasting styles without needing a separate styling product.

Figure 8:
FIG. 8 illustrates the blowout stylability performance of hair washed with conditioner comprising 5% cationic polyurethane as described herein. The style on the left, which was done on hair treated with the conditioner containing cationic WBPU, shows better body and shape after styling with a round brush—the hair curls naturally where the brush was used, which is a desirable effect of a blowout style. The blowout style done on the hair treated with conditioner alone (right) has less style definition, more frizziness, and less volume. A blinded, trained sensory evaluator determined that the style obtained using conditioner containing cationic WBPU was aesthetically preferable to the style obtained using the conditioner alone.

In addition to curl hold, conditioners containing the disclosed cationic polyurethanes can provide hold and stylability for blowout styles in which a stylist brushes the hair while blow drying in order to provide bounce, body and shape to the hair. FIG. 8, for example, shows the superior stylability of hair washed with a conditioner containing a cationic polyurethane PU 363 (left) vs. hair washed with a conditioner without a cationic WBPU (right).

Figure 9:
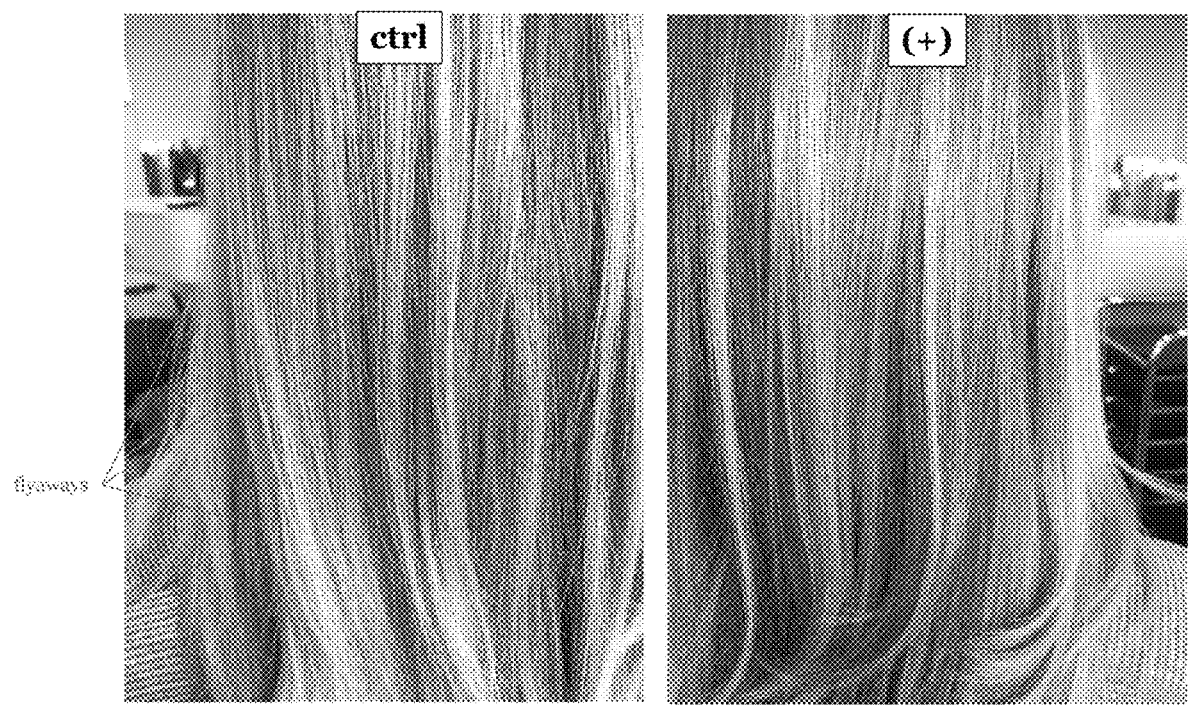
FIG. 9 shows minimization of flyaways on hair treated with conditioner comprising 5% cationic polyurethane as described herein applied on the right side of the panelist. The hair treated with the conditioner comprising cationic polyurethane (right) lies smoother after drying and has improved shine and manageability. A blinded, trained sensory evaluator determined that this style obtained using conditioner containing cationic WBPU was aesthetically preferable to the style obtained using the conditioner alone.

The incorporation of the disclosed cationic polyurethanes into conditioner also improves the smooth appearance of hair and minimizes flyaways, presumably by providing a thin, stiff coating around the hair fiber and serving as a hydrophobic layer that helps hairs maintain their straight style after blow drying. FIG. 9, for example, shows that conditioner containing 5% amphoteric/cationic polyurethane PU 362 provides significant flyaway minimization (right) compared to control conditioner (left).

Figure 10:
FIG. 10 shows natural curl retention on hair treated with conditioner comprising 5% cationic polyurethane as described herein. The hair treated with the conditioner comprising cationic polyurethane (right) shows better natural curls enhancement and manageability compared to the hair treated with the conditioner alone, which was frizzier and had poor curl shape. A blinded, trained sensory evaluator determined that this style obtained using conditioner containing cationic WBPU was aesthetically preferable to the style obtained using the conditioner alone.
Figure 10:

Finally, conditioners containing cationic polyurethanes as described herein preserve curl shape in naturally curly-haired consumers. FIG. 10, for example, shows the relative curl enhancement that can be attained with use of the amphoteric/cationic polyurethane PU 362 conditioner (right), in contrast to the poor curl enhancement observed with use of a blank conditioner (left).

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

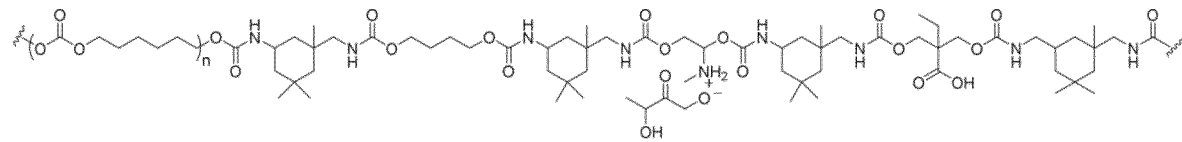

The invention claimed is:

1. A hair treatment composition comprising a cationic polyurethane, wherein
   (a) the cationic polyurethane is formed from W, V, Y, Z and X, wherein
      W is a polycarbonate polyol;
      V is a polyisocyanate;
      Y is a $C_{1-8}$ alkyldiol monomer;
      Z is a $C_{1-8}$ aminoalkyldiol monomer; and
      X is a neutralizing ion, wherein
      (i) the molecular weight of W is about 1,000 g/mol;
         the molar ratio of V:W is 1:0.18 to about 1:0.32;
         the molar ratio of V:Y is 1:0.24 to about 1:0.72; and
         the molar ratio of V:Z is 1:0.08 to about 1:0.47; or
      (ii) the molecular weight of W is about 2,000 g/mol;
         the molar ratio of V:W is 1:0.08 to about 1:0.18;
         the molar ratio of V:Y is 1:0.36 to about 1:0.82; and
         the molar ratio of V:Z is 1:0.08 to about 1:0.49; or
      (iii) the molecular weight of W is about 3,000 g/mol;
         the molar ratio of V:W is 1:0.05 to about 1:0.13;
         the molar ratio of V:Y is 1:0.4 to about 1:0.85; and
         the molar ratio of V:Z is 1:0.08 to about 1:0.49; or
   (b) the cationic polyurethane is formed from W, V, Y, Z, $Z^1$ and X, wherein
      W is a polycarbonate polyol;
      V is a polyisocyanate;
      Y is a $C_{1-8}$ alkyldiol monomer;
      Z is a $C_{1-8}$ aminoalkyldiol monomer;
      $Z^1$ is an ethoxylated polyol;
      X is a neutralizing ion, wherein
      (i) the molecular weight of W is about 1,000 g/mol;
         the molar ratio of V:W is 1:0.19 to about 1:0.33;
         the molar ratio of V:Y is 1:0.19 to about 1:0.7;
         the molar ratio of V:Z is 1:0.08 to about 1:0.49; and
         the molar ratio of V:$Z^1$ is 1:0 to about 1:0.03; or
      (ii) the molecular weight of W is about 2,000 g/mol
         the molar ratio of V:W is 1:0.09 to about 1:0.18;
         the molar ratio of V:Y is 1:0.31 to about 1:0.8;
         the molar ratio of V:Z is 1:0.09 to about 1:0.51; and
         the molar ratio of V:$Z^1$ is 1:0 to about 1:0.03; or
      (iii) the molecular weight of W is about 3,000 g/mol
         the molar ratio of V:W is 1:0.05 to about 1:0.13;
         the molar ratio of V:Y is 1:0.36 to about 1:0.83;
         the molar ratio of V:Z is 1:0.09 to about 1:0.52; and
         the molar ratio of V:$Z^1$ is 1:0 to about 1:0.03; or
   (c) the cationic polyurethane is formed from W, V, Y, Z, $Z^2$ and X, wherein
      W is a polycarbonate polyol;
      V is a polyisocyanate;
      Y is a $C_{1-8}$ alkyldiol monomer;
      Z is a $C_{1-8}$ aminoalkyldiol monomer;
      $Z^2$ is a hydroxylated alkyl acid monomer;
      X is a neutralizing ion, wherein
      (i) the molecular weight of W is about 1,000 g/mol;
         the molar ratio of V:W is 1:0.19 to about 1:0.33;
         the molar ratio of V:Y is 1:0.14 to about 1:0.44;
         the molar ratio of V:Z is 1:0.08 to about 1:0.47; and
         the molar ratio of V:$Z^2$ is 1:0.05 to about 1:0.33; or (ii) the molecular weight of W is about 2,000 g/mol;
the molar ratio of V:W is 1:0.09 to about 1:0.18;
the molar ratio of V:Y is 1:0.26 to about 1:0.53;
the molar ratio of V:Z is 1:0.09 to about 1:0.49; and
the molar ratio of V:$Z^2$ is 1:0.05 to about 1:0.35; or
(iii) the molecular weight of W is about 3,000 g/mol;
the molar ratio of V:W is 1:0.05 to about 1:0.13;
the molar ratio of V:Y is 1:0.3 to about 1:0.56;
the molar ratio of V:Z is 1:0.09 to about 1:0.5; and
the molar ratio of V:$Z^2$ is 1:0.05 to about 1:0.35.

2. The composition of claim 1, wherein the cationic polyurethane is formed from W, V, Y, Z and X, wherein
the molecular weight of W is about 1,000 g/mol;
the molar ratio of V:W is 1:0.18 to about 1:0.32;
the molar ratio of V:Y is 1:0.24 to about 1:0.72; and
the molar ratio of V:Z is 1:0.08 to about 1:0.47.

3. The composition of claim 1, wherein the cationic polyurethane is formed from W, V, Y, Z and X, wherein
the molecular weight of W is about 2,000 g/mol;
the molar ratio of V:W is 1:0.08 to about 1:0.18;
the molar ratio of V:Y is 1:0.36 to about 1:0.82; and
the molar ratio of V:Z is 1:0.08 to about 1:0.49.

4. The composition of claim 1, wherein the cationic polyurethane is formed from W, V, Y, Z and X, wherein
the molecular weight of W is about 3,000 g/mol;
the molar ratio of V:W is 1:0.05 to about 1:0.13;
the molar ratio of V:Y is 1:0.4 to about 1:0.85; and
the molar ratio of V:Z is 1:0.08 to about 1:0.49.

5. The composition of claim 1, wherein the cationic polyurethane is formed from W, V, Y, Z, $Z^1$ and X, wherein
the molecular weight of W is about 1,000 g/mol;
the molar ratio of V:W is 1:0.19 to about 1:0.33;
the molar ratio of V:Y is 1:0.19 to about 1:0.7;
the molar ratio of V:Z is 1:0.08 to about 1:0.49; and
the molar ratio of V:$Z^1$ is 1:0 to about 1:0.03.

6. The composition of claim 1, wherein the cationic polyurethane is formed from W, V, Y, Z, $Z^1$ and X, wherein
the molecular weight of W is about 2,000 g/mol
the molar ratio of V:W is 1:0.09 to about 1:0.18;
the molar ratio of V:Y is 1:0.31 to about 1:0.8;
the molar ratio of V:Z is 1:0.09 to about 1:0.51; and
the molar ratio of V:$Z^1$ is 1:0 to about 1:0.03.

7. The composition of claim 1, wherein the cationic polyurethane is formed from W, V, Y, Z, $Z^1$ and X, wherein
the molecular weight of W is about 3,000 g/mol
the molar ratio of V:W is 1:0.05 to about 1:0.13;
the molar ratio of V:Y is 1:0.36 to about 1:0.83;
the molar ratio of V:Z is 1:0.09 to about 1:0.52; and
the molar ratio of V:$Z^1$ is 1:0 to about 1:0.03.

8. The composition of claim 1, wherein the cationic polyurethane is formed from W, V, Y, Z, $Z^2$ and X, wherein
the molecular weight of W is about 1,000 g/mol;
the molar ratio of V:W is 1:0.19 to about 1:0.33;
the molar ratio of V:Y is 1:0.14 to about 1:0.44;
the molar ratio of V:Z is 1:0.08 to about 1:0.47; and
the molar ratio of V:$Z^2$ is 1:0.05 to about 1:0.33.

9. The composition of claim 1, wherein the cationic polyurethane is formed from W, V, Y, Z, $Z^2$ and X, wherein
the molecular weight of W is about 2,000 g/mol;
the molar ratio of V:W is 1:0.09 to about 1:0.18;
the molar ratio of V:Y is 1:0.26 to about 1:0.53;
the molar ratio of V:Z is 1:0.09 to about 1:0.49; and
the molar ratio of V:$Z^2$ is 1:0.05 to about 1:0.35.

10. The composition of claim 1, wherein the cationic polyurethane is formed from W, V, Y, Z, $Z^2$ and X, wherein
the molecular weight of W is about 3,000 g/mol;
the molar ratio of V:W is 1:0.05 to about 1:0.13;
the molar ratio of V:Y is 1:0.3 to about 1:0.56;
the molar ratio of V:Z is 1:0.09 to about 1:0.5; and
the molar ratio of V:$Z^2$ is 1:0.05 to about 1:0.35.

11. The composition of claim 1, wherein the cationic polyurethane is a salt of the formula:

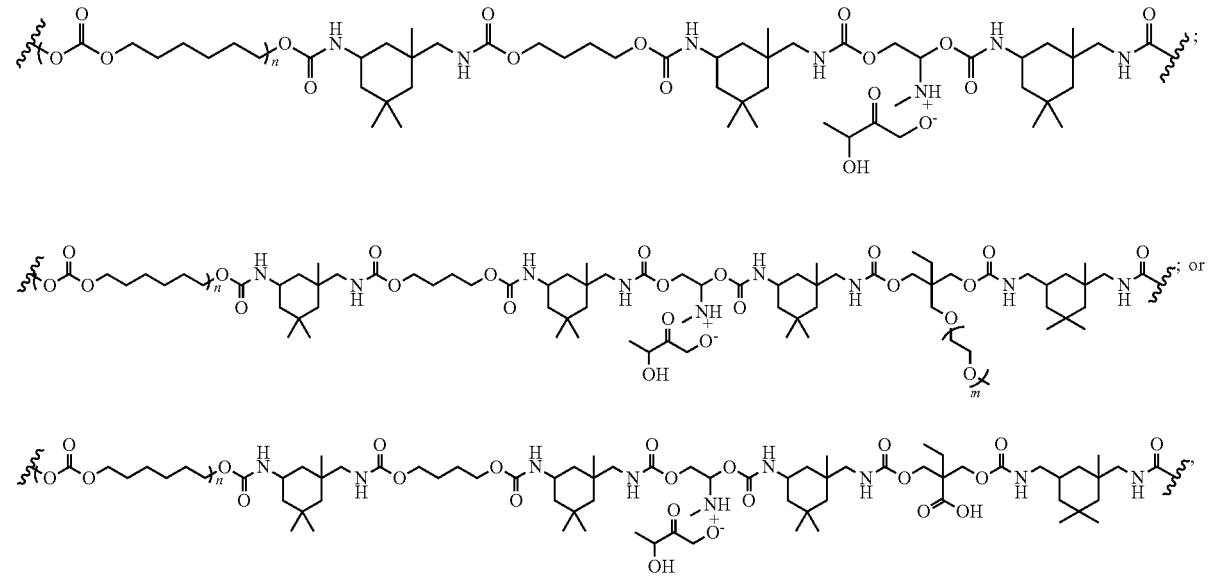

wherein n is 6 to 21 and m is 19 to 31.

12. The composition of claim 1, wherein the cationic polyurethane is dispersed in water.

13. The composition of claim 1, wherein the composition further comprises a neutralizer.

14. The composition of claim 1, wherein the composition further comprises an oil.

15. The composition of claim 11, wherein the oil is linoleic acid or a mixture of fatty acids.

16. A method for styling hair comprising
applying the cationic polyurethane based composition according to claim 1 to the hair.

\* \* \* \* \*

UNITED STATES PATENT AND TRADEMARK OFFICE
CERTIFICATE OF CORRECTION

Page 1 of 2

PATENT NO. : 10,987,300 B2
APPLICATION NO. : 16/128620
DATED : April 27, 2021
INVENTOR(S) : Soo-Young Kang et al.

It is certified that error appears in the above-identified patent and that said Letters Patent is hereby corrected as shown below:

In Claim 11, at Columns 21 and 22, please replace the formulas below:

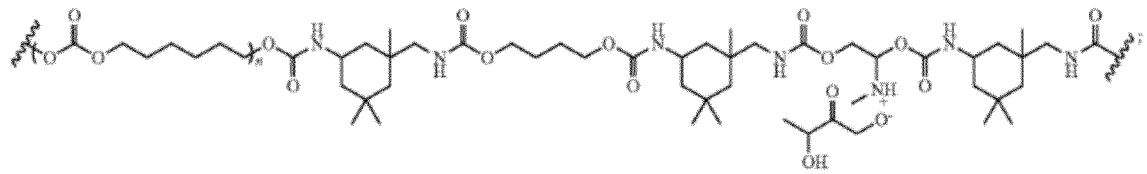

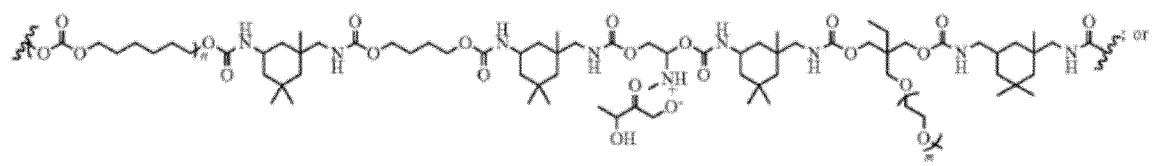

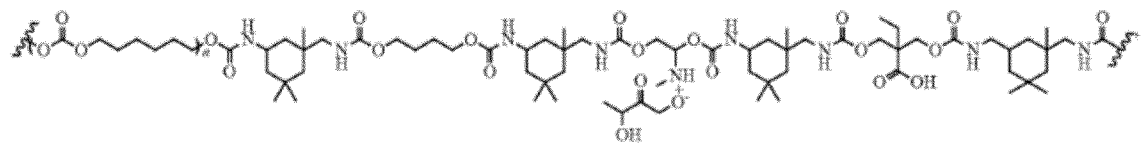

,

With the following formulas:

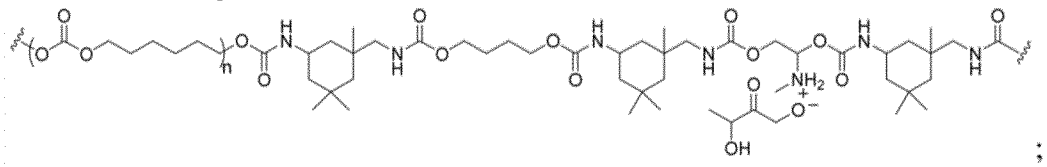

;

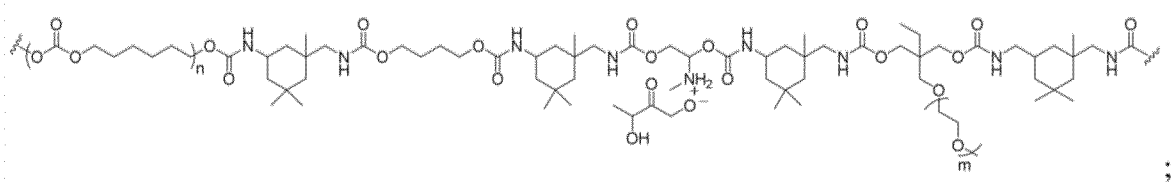

;

Signed and Sealed this
Eighth Day of June, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,987,300 B2 or